United States Patent
Baba et al.

(10) Patent No.: US 7,517,441 B2
(45) Date of Patent: Apr. 14, 2009

(54) ELECTROPHORETIC BUFFER

(75) Inventors: Yoshinobu Baba, Tokushima (JP); Kazunori Kataoka, Tokyo (JP); Mari Tabuchi, Tokushima (JP); Yukio Nagasaki, Ibaraki (JP); Yasuko Tanaka, Marugame (JP); Chie Kuwahara, Yokohama (JP)

(73) Assignee: Japan Science and Technology Agency, Kawaguchi-shi (JP)

( * ) Notice: Subject to any disclaimer, the term of this patent is extended or adjusted under 35 U.S.C. 154(b) by 831 days.

(21) Appl. No.: 10/507,624

(22) PCT Filed: Mar. 13, 2003

(86) PCT No.: PCT/JP03/02969

§ 371 (c)(1),
(2), (4) Date: Sep. 14, 2004

(87) PCT Pub. No.: WO03/078993

PCT Pub. Date: Sep. 25, 2003

(65) Prior Publication Data

US 2006/0040396 A1     Feb. 23, 2006

(30) Foreign Application Priority Data

Mar. 15, 2002    (JP) .............................. 2002-072412

(51) Int. Cl.
*G01N 27/447*    (2006.01)
(52) U.S. Cl. .................. 204/455; 204/451; 204/456
(58) Field of Classification Search .................. 422/100
See application file for complete search history.

(56) References Cited

U.S. PATENT DOCUMENTS

| | | | |
|---|---|---|---|
| 5,468,365 A | 11/1995 | Menchen et al. | |
| 5,482,608 A | 1/1996 | Keely et al. | |
| 6,375,817 B1 * | 4/2002 | Taylor et al. | 204/453 |

FOREIGN PATENT DOCUMENTS

| | | |
|---|---|---|
| JP | 6-242073 A | 9/1994 |
| JP | 8-506655 A | 7/1996 |
| JP | 10-110019 A | 4/1998 |
| JP | 10-195152 A | 7/1998 |
| JP | 10195152 A * | 7/1998 |
| JP | 11-118761 A | 4/1999 |

OTHER PUBLICATIONS

Nakamura et al., "Aggregate of Amphiphilic Block Copolymer as a Pseudo-Stationary Phase in Capillary Electrophoresis," Analytical Sciences, Sep. 1999, vol. 15, pp. 879-883.*

* cited by examiner

*Primary Examiner*—Alex Noguerola
(74) *Attorney, Agent, or Firm*—Birch, Stewart, Kolasch & Birch, LLP

(57) ABSTRACT

By using an electrophoretic buffer comprising a polymerized polymer micelle formed by the steps comprising dispersing into an aqueous medium a block copolymer represented by HPLS-HPBS-PLZA, wherein HPLS is a hydrophilic polymer segment, HPBS is a hydrophobic polymer segment, and PLZA is a polymerizable group having an ethylenically unsaturated double bond, and polymerizing the block copolymer as a buffer for a capillary electrophoresis or a microchip electrophoresis, pressurizing the sample after introduction at a given pressure for a given time period, and electrophoresing in an electrophoretic electric field, a polymer compound such as DNA can be separated rapidly and in high separation ability.

14 Claims, 26 Drawing Sheets

ELECTROPHORETIC BUFFER

This application is a 371 of PCT/JP03/02969, filed on Mar. 13, 2003, which claims foreign priority from Japanese application 2002-72412, filed on Mar. 15, 2002.

TECHNICAL FIELD

The present invention relates to an electrophoretic buffer and an electrophoresis method, which is capable of separating a polymer compound rapidly and at high separation ability.

BACKGROUND ART

The existing electrophoretic buffer is excellent in separation ability to a limited size. However, since a polymer having a high viscosity (methylcellulose, hydroxylcellulose, polyacrylamide or the like) is used as a buffer, there are some defects 1) that it takes time to inject the buffer into a microchannel, 2) that the injection becomes more difficult, as a channel width becomes narrower, 3) that it is necessary to change a polymer concentration depending on a size of a DNA, and there is a limitation of a separation degree to separation of a wide range of a DNA size, 4) that viscosity of the buffer is sensitive to temperature, and the like. Therefore, there is desired an electrophoretic buffer which does not have the problems of the above-mentioned 1) to 4) and is capable of separating a polymer compound rapidly and at high separation ability. In addition, there is desired an electrophoresis method which is capable of separating a polymer compound rapidly and at high separation ability.

DISCLOSURE OF INVENTION

An object of the present invention is to provide an electrophoretic buffer and an electrophoresis method, which is capable of separating a polymer compound rapidly and at high separation ability.

Specifically, the gist of the present invention relates to:

[1] an electrophoretic buffer comprising a polymerized polymer micelle formed by:

dispersing into an aqueous medium a block copolymer represented by the general formula (1):

HPLS-HPBS-PLZA                               (1)

wherein HPLS is a hydrophilic polymer segment, HPBS is a hydrophobic polymer segment, and PLZA is a polymerizable group having an ethylenically unsaturated double bond, and polymerizing the block copolymer;

[2] an electrophoretic method characterized in migrating a sample containing a polymer compound in the presence of the electrophoretic buffer of [1];

[3] a capillary electrophoresis method comprising the steps of:

(a) injecting a sample containing a polymer compound into a capillary by electric injection at 1 to 30 kV for 1 to 60 seconds, or pressurizing injection at 0.2 to 5 kPa for 2 to 60 seconds, to migrate the sample under an electrophoretic electric field capable of separating the polymer compound; and (b) pressurizing at 0.2 to 10 kPa for 2 to 60 seconds, and migrating the polymer compound by an electrophoretic electric field;

[4] a microchip electrophoresis method wherein a microchip comprises a loading channel, and a separating channel intersecting with the loading channel, wherein a sample reservoir is provided on one end of the loading channel, and an outlet is provided on the other end of the loading channel, the electrophoretic method comprising the steps of:

(a) supplying a sample containing a polymer compound to the sample reservoir;

(b) pressurizing the loading channel at 5.5 to 7 kPa for 0.1 to 5 seconds, thereby migrating the polymer compound in the sample reservoir to the intersecting portion of the loading channel and the separating channel; and (c) pressurizing the separating channel at 1 to 10 kPa for 0.1 to 5 seconds, and migrating the polymer compound by an electrophoretic electric field in the separating channel.

BRIEF DESCRIPTION OF THE DRAWINGS

The numerals used in the drawings are as follows.
1 peak of 100 bp DNA
2 peak of 200 bp DNA
3 peak of 300 bp DNA
4 peak of 400 bp DNA
5 peak of 500 bp DNA
6 peak of 600 bp DNA
7 peak of 700 bp DNA
8 peak of 800 bp DNA
9 peak of 900 bp DNA
10 peak of 1 kbp DNA
11 peak of 1.1 kbp DNA
12 peak of 1.2 kbp DNA
13 peak of 1.3 kbp DNA
14 peak of 1.4 kbp DNA
15 peak of 1.5 kbp DNA

BEST MODE FOR CARRYING OUT THE INVENTION

Figure 1:
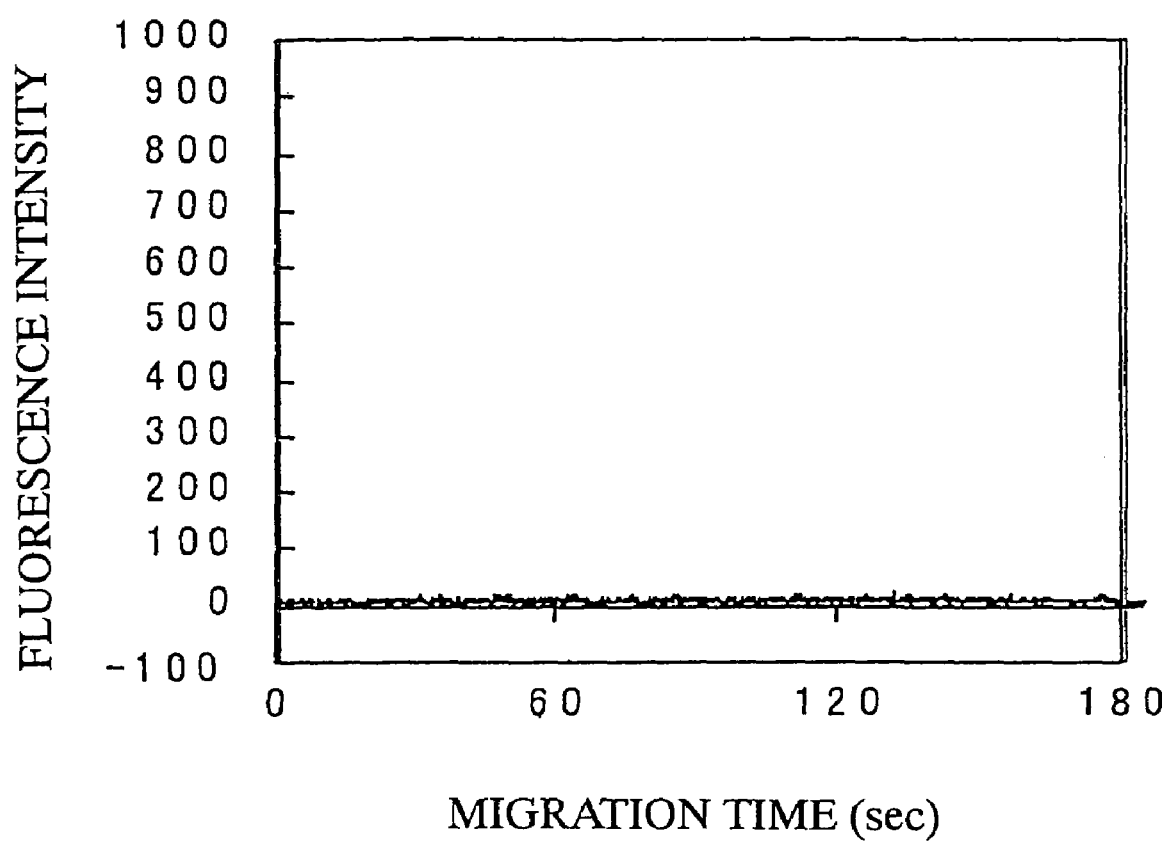
FIG. 1 is a diagram showing the results for studying electrophoretic conditions in a microchip electrophoresis.

One of the significant features of the electrophoretic buffer of the present invention residues in that the buffer comprises a polymerized polymer micelle formed by:

dispersing into an aqueous medium a block copolymer represented by the general formula (1):

HPLS-HPBS-PLZA    (1)

wherein HPLS is a hydrophilic polymer segment, HPBS is a hydrophobic polymer segment, and PLZA is a polymerizable group having an ethylenically unsaturated double bond, and polymerizing the block copolymer.

The electrophoretic buffer of the present invention is characterized that the buffer has a low viscosity as compared with the buffer which has been usually used in the conventional capillary electrophoresis or microchip electrophoresis. Therefore, the electrophoretic buffer of the present invention has an advantage that the buffer can be smoothly injected into a microchannel or a capillary, and that a buffer injecting time can be shortened. In addition, even when a channel width becomes narrower, the buffer injection is made easy. Using the buffer of the present invention, nucleic acids having a short base size (for instance, 2 to 200 bp or the like) which could be conventionally analyzed only with a buffer having a high viscosity, can be reproducibly analyzed. In the conventional buffer, the viscosity of the buffer has to be changed depending upon a size of each nucleic acid. However, since the buffer of the present invention can be used in a wide range of sizes of nucleic acids, nucleic acids having different sizes can be analyzed simultaneously. In addition, the buffer of the present invention has an advantage that the buffer is not influenced by a change in viscosity due to temperature, and an error between days due to an atmospheric temperature or room temperature is less likely to be generated.

In the present specification, the polymer compound includes proteins, peptides, amino acids, sugars, polysaccharides, nucleic acids (for instance, DNA, RNA and the like), and the like. The above-mentioned nucleic acids may be single-stranded or double-stranded.

Regarding a moiety composed of HPLS-HPBS (hydrophilic polymer segment-hydrophobic polymer segment) in the above-mentioned general formula (1), the kinds of polymers constituting each segment (for instance, polymerization degree, raw material monomer or the like) are not limited, as long as the moiety itself forms a polymer micelle in an aqueous medium. Therefore, in the present specification, the term "polymer" is used so as to encompass the concept of an oligomer.

In the HPLS-HPBS moiety in the above-mentioned general formula (1), a group PLZA, that is, a polymerizable group having an ethylenically unsaturated double bond, is covalently bound to an end of a hydrophobic polymer segment (opposite side of binding to HPLS). The functional group as described above may be any functional group as long as the group has no adverse influences on micelle forming ability of the HPLS-HPBS moiety.

The polymer constituting HPLS includes, but not limited to, polyethylene glycol, polyvinyl alcohol, poly(meth)acrylic acid, polyvinylpyridine, polyacrylamide, polydimethyl acrylamide, polymethyl vinyl ether, and the like. The polymer constituting HPBS includes, but not limited to, polylactide, polyglycolide, poly(butyrolactone), poly(valerolactone), polypropylene glycol, poly($\alpha$-amino acid), poly(methyl methacrylate), poly(ethyl methacrylate), polystyrene, poly($\alpha$-methylstyrene), polyisoprene, polybutadiene, polyethylene, polypropylene and polyvinyl acetate.

Among them, as the HPLS, polyethylene glycol is especially preferable from the viewpoint of micelle forming ability. In addition, as the HPBS, polylactide is especially preferable from the viewpoint of micelle forming ability.

The above-mentioned PLZA may be any one as long as the PLZA is capable of polymerizing in an aqueous medium. The PLZA includes, for instance, (meth)acryloyl, crotyl, vinylcarbonylamino ($CH_2$=CHCONH—; acrylamide group), isopropenylcarbonylamino [$CH_2$=C($CH_3$)CONH—; methacrylamide group], vinyloxycarbonyl ($CH_2$=CHOCO—), p-vinylbenzyl ($CH_2$=CH—$C_6H_4$—$CH_2$—), p-isopropenylbenzyl ($CH_2$=C($CH_3$)—$C_6H_4$—$CH_2$—), p-isopropenylphenyl ($CH_2$=CH—$CH_2$—), vinyl ($CH_2$=CH—) group, and the like.

Among them, as the PLZA, (meth)acryloyl is especially preferable from the viewpoint of stable polymerization formation.

Specific examples of the block copolymer represented by the general formula (1) include methoxy-polyethylene glycol/polylactide-methacryloyl, methoxy-polyvinyl alcohol/polyglycoside-crotyl, and methoxy-poly(meth)acrylic acid/polybutyllactone-vinyloxycarobonylmethoxy-polyacrylamide/polystyrene-p-vinylbenzyl. Among the above-mentioned specific examples, methoxy-polyethylene glycol/polylactide-methacryloyl is especially preferable from the viewpoint of stable micelle formation.

These block copolymers represented by the general formula (1) may be those prepared by any known per se method. Preferably, the block copolymers can be prepared by first forming HPLS by a so-called living anion polymerization using respective corresponding monomers, polymerizing a monomer corresponding to HPBS directly in the reaction system, and further adding a halide or an acid anhydride, having an ethylenically unsaturated double bond to introduce a PLZA group. The polymerization method as described above is suitable for preparing a block copolymer in which each segment has a desired molecular weight. Specifically, as to the molecular weight of the block copolymer, the molecular weight of HPLS is from 500 to 50,000, preferably from 3,000 to 8,000, and the molecular weight of HPBS is from 500 to 80,000, preferably from 3,000 to 8,000. Molecular weights of each of these segments can be determined by gel permeation chromatography.

The block copolymer of the general formula (1) thus prepared can be formed into a polymer micelle by dispersing into an aqueous medium (for instance, water or an aqueous solution buffered with an appropriate buffer) in a given concentration.

The molecular weight of each segment which is optimal for forming the micelle described above cannot be limited because the molecular weight varies depending upon the kinds of a hydrophilic polymer chain and a hydrophobic polymer chain, and a combination of those chains. However, a person skilled in the art can determine an optimal molecular weight of each segment by actually preparing a block copolymer and evaluating its micelle forming ability without requiring undue experimentation. When a block copolymer having polyethylene glycol (or polyoxyethylene) as a hydrophilic polymer segment, and polylactide as a hydrophobic polymer segment, which is an especially preferable embodiment, is taken as an example, the molecular weight of the former is generally from 500 to 50,000, preferably from 3,000 to 8,000, especially preferably from 5,500 to 6,500, and the molecular weight of the latter is generally from 500 to 80,000, preferably from 3,000 to 8,000, especially preferably from 4,000 to 4,500.

In accordance with the present invention, the polymer micelle thus obtained can be prepared by polymerization utilizing a polymerizable group having an ethylenically unsaturated double bond covalently bound to an end of a hydrophobic polymer segment in the presence of an appropriate polymerization initiator in the state of a reaction mixture, or in the state where the polymer micelle is suspended again in an aqueous medium after being isolated from the reaction mixture. As the polymerization initiator, any kind of the polymerization initiator can be utilized as long as the polymerization initiator is capable of polymerizing the polymerizable group in an aqueous medium. Generally, it is preferable to use a radical polymerization initiator. The initiator as described above includes peroxides, azo compounds and redox initiators. Alternatively, the above-mentioned polymerization may be initiated using light or radiation.

In the electrophoretic buffer of the present invention, a polymerized polymer micelle formed by further adding a low-molecular polymerizable monomer to the block copolymer represented by the general formula (1), and polymerizing the block copolymer can be also suitably used. This embodiment has an advantage that a polymerized polymer micelle can be efficiently prepared by adding a low-molecular weight polymerizable monomer (for instance, styrene, methyl (meth)acrylate, vinyl acetate, $\alpha$-c methylstyrene, a dialkyl (meth)acrylamide, methylenebisacrylamide, ethylene glycol bis(meth)acrylate or the like) to the block copolymer represented by the general formula (1) to polymerize.

The polymerized polymer micelle thus obtained can retain the shape of a precursor polymer micelle almost as it is, and stably retain the form of a micelle at any concentration in an aqueous medium, so that the polymerized polymer micelle can be suitably used in an electrophoretic buffer.

The content of the polymerized polymer micelle of the present invention in the electrophoretic buffer of the present invention is from 1 to 20 mg/ml, more preferably from 5 to 10 mg/ml from the viewpoint of obtaining high separation ability for substances to be determined.

The diluent for diluting the above-mentioned micelle includes buffers which are generally used as an electrophoretic buffer for a polymer compound, such as water, Tris-glycine buffer, Tris-glycine buffer, Tris-borate buffer, Tris-hydrochloric acid buffer, Tris-tricine buffer, Tris-sodium hydrogenphosphate buffer, Tris-borate-EDTA buffer and the like. As water for dilution or water for preparing a buffer, water which is usually used in electrophoresis such as ultra-pure water, deionized water, and Milli Q water are used, and Milli Q water is especially preferable.

When a polymer compound to be tested is a protein or a peptide, in addition to the block copolymer of the general formula (1), there can be added sodium dodecylsulfate (SDS), or when a polymer compound to be tested is a peptide, Triton X-100, $\epsilon$-aminocaproic acid, 3-(C3-colamidopropyl)-dimethylamino)-1-propane, CHAPS, 6 to 8 M urea, tetramethylethylenediamine (TEMED), hexyltrimethylammonium bromide (HTAB), or the like can be added in addition to the above-mentioned block copolymer of the general formula (1).

When a polymer compound to be tested is a protein, the pH of the electrophoretic buffer of the present invention is preferably from 2 to 9, more preferably from 6.8 to 8.6, from the viewpoints of suitable electrophoresis and normal peak separation. When a polymer compound to be tested is a peptide, the pH is preferably from 2 to 11, more preferably from 2.5 to 3.1. When a compound to be tested is nucleic acids, the pH is preferably from 6.8 to 9.2, more preferably from 7.5 to 8.5, from the viewpoints of suitable electrophoresis and normal peak separation.

The electrophoretic buffer of the present invention is prepared by appropriately diluting the polymerized polymer micelle of the present invention with the above-mentioned dilution buffer, and then adjusting the pH with sodium hydroxide or the above-mentioned buffer.

The electrophoresis method of the present invention includes a method characterized in electrophoresing a sample containing a polymer compound in the presence of the above-mentioned electrophoretic buffer. Here, the technique of electrophoresis is not particularly limited, and the present invention can be applied to various techniques. Among them, the present invention is especially suitably used in capillary electrophoresis, microchip electrophoresis and nanochannel electrophoresis.

More specifically, the electrophoresis method of the present invention, comprises in capillary electrophoresis, (a) injecting a sample containing a polymer compound into a capillary to migrate the sample under an electrophoretic electric field capable of separating the polymer compound, and (b) pressurizing inside the capillary, and migrating the polymer compound by an electrophoretic electric field.

The step of injecting the sample into a capillary to migrate the polymer compound under an electrophoretic electric field capable of separating the polymer compound is more specifically carried out by voltage method, pressurizing method or dropping method, and the magnitude of the voltage and applied pressure and the time during the method are properly determined depending upon the kinds of the apparatus, the thickness (inner diameter), the length of the capillary, and the like. From the viewpoints of obtaining rapid separation and high separation ability, and accomplishing higher sensitive detection, it is especially preferable to inject the sample containing a polymer compound into the capillary by electric injection or pressurizing injection at 1 to 30 kV for 1 to 60 seconds, preferably pressurizing injection at 0.2 to 5 kPa, more preferably 1 kPa to migrate the sample under an electrophoretic electric field capable of separating the polymer compound. Here, it is desired that the above-mentioned pressurization is carried out for preferably 2 to 60 seconds, more preferably from 5 to 10 seconds, especially preferably from 7 to 8 seconds. Thereafter, from the viewpoint of accomplishing rapid separation while retaining high separation ability, it is desired that the pressurization, preferably pressurization at 0.2 to 10 kPa, more preferably at 1 kPa, is carried out before the step of migrating a polymer compound by an electrophoretic electric field. Here, it is desired that the above-mentioned pressurization is carried out for preferably 2 to 60 seconds, more preferably 5 to 10 seconds, especially preferably 7 to 8 seconds.

In the present specification, the unit for pressure (kPa) in the capillary electrophoresis means a force which is applied at an inlet for injecting a sample.

In the capillary usable in the capillary electrophoresis, the inner diameter, the outer diameter, the full length, the effective length are not particularly limited, and those of usually used sizes can be used. As to the effective length, a capillary having a short effective length can be used, from the viewpoint of enabling analysis rapidly. The effective length of the capillary as used herein refers to a distance between an inlet for injecting a sample and a detection part.

It is desired that the electrophoretic electric field in the capillary electrophoresis is preferably from 20 V/cm to 10 kV/cm, more preferably from 50 V/cm to 5 kV/cm, especially preferably from 100 V/cm to 1 kV/cm, from the viewpoints of obtaining an excellent separation ability and shortening the migration time.

In the microchip electrophoresis, there is used a microchip comprising a loading channel and a separating channel intersecting with the loading channel, wherein a sample reservoir is provided on one end of the loading channel, and an outlet is provided on the other end of the loading channel.

In the microchip electrophoresis, the electrophoresis method of the present invention specifically comprises the steps of:
(a) supplying a sample containing a polymer compound to a sample reservoir,
(b) migrating the polymer compound in the sample reservoir to an intersection portion of the loading channel and the separation channel by pressurization, and
(c) pressurizing the separation channel, and migrating the polymer compound in the separation channel.

The step of supplying the sample to the sample reservoir is more specifically accomplished by loading a sample to the sample reservoir in an amount of preferably from 1 to 10 µl, more preferably from 2 to 5 µl.

It is desired that the step of migrating the sample in the sample reservoir to the intersection portion of the loading channel and the separation channel is carried out by migrating the sample to the intersection portion of the loading channel and the separation channel from the sample reservoir under the condition that the electrophoresis buffer is not set at the outlet by pressurizing, preferably pressurizing at 3 to 7 kPa, more preferably at 5 to 7 kPa, especially preferably at 5.5 to 7 kPa, from the viewpoint of obtaining sufficient detection sensitivity. Here, it is desired that the above-mentioned pressurization is carried out for preferably 0.1 to 5 seconds, more preferably 0.5 to 2 seconds, especially preferably 1 second.

The unit of pressure (kPa) in the microchip electrophoresis as used herein means a force applied at a pressure loading port of the separation channel.

It is desired that the step of migrating the sample in the separation channel is more specifically carried out by pressurizing a separation channel, preferably pressurizing at 1 to 10 kPa, more preferably at 3.5 to 10 kPa, especially preferably at 5 to 7 kPa, and thereafter migrating the sample by an electrophoretic voltage, from the viewpoint of obtaining high separation ability more rapidly. Here, it is desired that the above-mentioned pressurization is carried out for preferably 0.1 to 5 seconds, more preferably 0.5 to 2 seconds, especially preferably 1 second.

The materials for the microchip include, for instance, silica glass, borosilicate glass, soda glass, polymethyl methacrylate, polycarbonate, dimethylsiloxane and the like. Among them, glass or polymethyl methacrylate is desired, from the viewpoints of little adsorption of the sample and facilitation of the chip working. In addition, there may be used those of which inner wall is subjected to a process similar to that of the capillary electrophoresis.

In the microchip electrophoresis, the size of the microchip is, for instance, a length of from 10 to 120 mm, a width of from 10 to 120 mm, and a thickness of from 500 to 5000 µm.

Each of the shapes of the loading channel and the separating channel in the microchip is not particularly limited. There can be also used a chip in which 3 to 96 of the above-mentioned channels are arranged on a single piece of chip, capable of simultaneously analyzing the multi-channels. The manner of arrangement of the multi-channel includes parallel, radial, circular and the like, and its shape is not particularly limited.

The width of the above-mentioned channel can be properly set depending upon the size of the microchip and its purpose of use. Specifically, it is desired that the width of the channel is 0.1 µm or more, preferably 10 µm or more, from the viewpoint of obtaining a satisfactory analytical sensitivity, and that the width is 100 µm or less, preferably 50 µm or less, from the viewpoint of obtaining a satisfactory analytical accuracy. In addition, the depth of the above-mentioned channel can be properly set depending upon the size of the microchip and its purpose of use. Specifically, it is desired that the depth is 0.1 µm or more, preferably 10 µm or more, from the viewpoint of obtaining a satisfactory analytical sensitivity, and that the depth is 100 µm or less, preferably 50 µm or less, from the viewpoint of obtaining a satisfactory analytical accuracy. Further, the length of the above-mentioned separating channel can be properly selected depending upon the size of the microchip, and the compound to be analyzed. It is desired to further extend the length of the effective length. The effective length refers to a distance between the channel intersecting portion and a detecting point of a high polymer (arranged on the separating channel). It is desired that the effective length is 0.1 mm or more, preferably 10 mm or more, from the viewpoint of obtaining a satisfactory separation ability, and that the effective length is 100 mm or less, preferably 50 mm or less, from the viewpoint of rapid separation.

In addition, the size of the above-mentioned reservoir can be properly set depending upon the volume of the sample. Specifically, it is desired that the diameter is 0.05 mm or more, preferably 3 mm or less, from the viewpoints of handling upon the introduction of the sample and the thickness of the electrode.

It is desired that the electrophoretic electric field in the microchip electrophoresis is from 20 V/cm to 50 kV/cm, more preferably from 50 V/cm to 20 kV/cm, especially preferably from 100 V/cm to 10 kV/cm from the viewpoints of obtaining an excellent separation ability and shortening the migration time.

In the microchip electrophoresis, it is desired that the amount (concentration) of the sample upon injection is from 0.1 ng/ml to 1 g/ml, preferably from 10 ng/ml to 100 mg/ml, more preferably from 0.1 µg/ml to 10 mg/ml when the sample is a peptide or a protein, from the viewpoint of obtaining an excellent separation ability. When the above-mentioned sample is a saccharide or polysaccharide, it is desired that the amount (concentration) of the sample upon injection is from 0.1 µg/ml to 10 g/ml, preferably from 1 mg/ml to 5 g/ml, more preferably from 100 mg/ml to 1 g/ml in the case where the sample is a peptide or a protein, from the viewpoint of obtaining an excellent separation ability. When the above-mentioned sample is nucleic acids, it is desired that the amount (concentration) of the sample upon injection is from 0.1 ng/ml to 500 µg/ml, preferably from 10 ng/ml to 100 µg/ml, more preferably from 100 ng/ml to 500 µg/ml in the case where the sample is a peptide or a protein, from the viewpoint of obtaining an excellent separation ability.

The nano-channel electrophoresis refers to electrophoresis which is carried out by using a chip in which a flow path having a channel width in the nanometer size of from 1 nm to 1 µm, preferably from 10 to 500 nm, more preferably from 50 to 100 nm is formed. This embodiment includes a case where a structural member of a nano-size mentioned above is formed on the channel of a micrometer size. The shape of the structural member of a nano-size includes, but not particularly limited to, for instance, those of square, circle, triangle and the like. The setting intervals of the structural members are also not particularly limited. The nano-channel chip constituted by these structural members is used. In the same manner as the case of the capillary electrophoresis, there is included a chip capable of simultaneously analyzing the multi-channels.

The channel in the nano-channel electrophoresis can have various designs, including those in which the shape of the channel having the feature of the nanometer size has a bent curvature, those of wound shape, those of zigzag shape, or a combination of those, and the like. By having the above shape, many channels can be formed in a micro-scale. Also, by having the above shape, a large number of samples can be processed at once, so that high throughput can be accomplished. In the case where the structural member of a nano-size is formed in the channel of the micrometer size, there are some advantages that its shape can be freely varied, and that its setting intervals can be freely changed. There can be carried out determination at multi-channels simultaneously.

Also in the nano-channel electrophoresis, as in the case of the microchip electrophoresis, there are included those comprising a loading channel, and a separating channel intersecting with the loading channel, wherein a sample reservoir is provided on one end of the loading channel, and an outlet is provided on the other end of the loading channel, and the shape is not particularly limited.

The materials for the nano-channel chip usable in the nano-channel electrophoresis may be the same ones as those in the microchip electrophoresis. The material includes, for instance, silica glass, borosilicate glass, soda glass, polymethyl methacrylate, polycarbonate, dimethylsiloxane, and the like.

As to the size of the nano-channel chip in the nano-channel electrophoresis, the same ones as those in the microchip electrophoresis can be applied. For instance, the nano-channel chip has a length of from 10 to 120 mm, a width of from 10 to 120 mm, and a thickness of from 500 to 5000 µm. The depth of the channel, the length of the channel, the size of the reservoir and the like of the nano-channel chip are in accordance with those of the microchip.

The present invention also relates to a capillary electrophoresis method, which comprises the steps of:
(a) injecting a sample containing a polymer compound into a capillary by electric injection at 1 to 30 kV for 1 to 60 seconds, or pressurizing injection at 0.2 to 5 kPa, more preferably at 1 kPa, to migrate the sample under an electrophoretic electric field capable of separating the polymer compound; and
(b) pressurizing at 0.2 to 10 kPa, more preferably 1 kPa, and migrating the polymer compound by an electrophoretic electric field.

Here, it is desired that the above-mentioned pressurization is carried out for 2 to 60 seconds, preferably 5 to 10 seconds, more preferably 7 to 8 seconds.

According to the above-mentioned capillary electrophoresis method, nucleic acids having a wide range of sizes (from 2 bp to 15 kbp) can be simultaneously analyzed and rapidly analyzed with a shorter sample injection time and high-sensitivity detection.

Conditions other than pressurization conditions are in accordance with the conditions of the above-mentioned capillary electrophoresis.

In the above-mentioned capillary electrophoresis method, various electrophoretic buffers can be used, which can be also used in combination with the electrophoretic buffer of the present invention.

In addition, the present invention relates to a microchip electrophoresis method, wherein a microchip comprises a loading channel, and a separation channel intersecting with the loading channel, wherein a sample reservoir is provided on one end of the loading channel, and an outlet is provided on the other end of the loading channel, comprising the steps of:
(a) supplying a sample containing a polymer compound into the sample reservoir;
(b) pressurizing the loading channel at 3 to 7 kPa, preferably 5 to 7 kPa, more preferably 5.5 to 7 kPa, thereby introducing the sample in the sample reservoir into the separation channel; and
(c) pressurizing the separation channel at 1 to 10 kPa, preferably 3.5 to 10 kPa, more preferably 5 to 7 kPa, and migrating the sample.

Here, it is desired that the above-mentioned pressurization is carried out for 0.1 to 5 seconds, preferably 0.5 to 2 seconds, more preferably 1 second.

According to the above-mentioned microchip electrophoresis method, nucleic acids having a wide range of sizes (from 2 bp to 15 kbp) can be simultaneously analyzed and rapidly analyzed with a shorter sample injection time and high-sensitivity detection.

Conditions other than pressurization conditions are in accordance with the conditions of the above-mentioned microchip electrophoresis.

In the above-mentioned microchip electrophoresis method, various electrophoretic buffers can be used, which can be also used in combination with the electrophoretic buffer of the present invention.

A fluorescent reagent for detecting nucleic acids includes ethidium bromide [510/595 (excitation wavelength/fluorescent wavelength, hereinafter the same)], ethidium homomixers-1 [528/617], Acridine orange [502/526], Thiazole orange (TO) [509/525], YO-PRO-1 [491/509], YO-PRO-3 [612/631], TO-PRO-1 [515/531], TO-PRO-3 [642/661], YO-YO-1 [491/509], TO-TO-1 [514/533], YO-YO-3 [612/631], TO-TO-3 [642/660], SYBR Green I [494/521], SYBR Green [254/520], SYBR Gold [300, 495/537], Oli Green (for ssDNA) [500/520], Ribo Green (for RNA) [500/525], FITC [494/519], 6-FAM [488/535], HEX [515/559], cy5 [649/670], cy3 [550/570], and the like. These fluorescent reagents are detected by using a capillary electrophoresis apparatus Beckman P/ACE [488/520 (excitation wavelength/detection wavelength, hereinafter the same)], a microchip electrophoresis apparatus Bioanalyzer (manufactured by Agilent Technologies) [635/670-700], cosmo-i SV1100 (manufactured by Hitachi Electronics) [472/585], and cosmo-i SV2100 (manufactured by Hitachi Electronics) [635/660].

The detection method of a protein subjected to electrophoresis includes, for instance, detection by absorption by UV wavelength light, fluorescent light, laser, lamp, LED or the like, electrochemical detection, chemiluminescent detection and the like. Specifically, in the case of a protein or peptide, the protein or peptide can be detected by determining the absorption at 200 nm; reacting SYPRO Orange with the protein or peptide, exciting at 460 to 550 nm, and determining a fluorescent light at 550 to 650 nm; or reacting the protein with a fluorescent marker (Agilent Technologies No. 5065-4430), exciting at 630 to 650 nm, and determining a fluorescent light at 670 to 700 nm; and electrochemical determination, chemiluminescent determination; and the like.

In the capillary electrophoresis, for instance, a device capable of emitting UV wavelength light and a detector of the UV wavelength light may be placed in the outlet of the capillary, or a device capable of emitting fluorescent wavelength and a detector of the fluorescent wavelength may be placed in the outlet.

In the microchip electrophoresis, for instance, a detector of the UV wavelength light may be placed in a detection point arranged on the separating channel, or a device capable of emitting fluorescent wavelength and a detector of the fluorescent wavelength may be placed in the detection point. Also, multi-channels can be detected simultaneously.

In the nano-channel electrophoresis, the same detector and the detection method as those of the microchip electrophoresis may be applied. Further, in the nano-channel electrophoresis, upon simultaneously detecting multi-channels, a larger number of samples can be simultaneously detected than the case of the microchip electrophoresis.

In the detection, when the identification of a protein, a peptide, an amino acid or the like is carried out, the identification can be carried out by UV absorption, the molecular weight marker, the migration time compared to the preparation, analyzing mass spectrum or the like.

According to the electrophoresis method of the present invention, since high separation ability can be obtained rapidly, the method is useful in PCR analysis of gene, cancer gene diagnostic analysis, SNPs analysis by SSCP, VNTR analysis, PCR-RFLP analysis, microsatellite analysis, applications to analyses of various diseases such as dementia, muscular dystrophy, cardiac disease, cardiac infarct, Down's syndrome, infection, diabetes, phenylketonuria and the like, and high throughput screening analysis of a protein or a sugar chain in proteosome analysis or glycosome analysis, so that there are expected applications to a medical clinical apparatus, and applications to elucidation of a biological function, a disease development mechanism and the like.

EXAMPLES

Preparation of Polymerized Polymer Micelle

One-hundred-and-thirty millimoles, 6.5 mL, of ethylene glycol was polymerized together with 30 mL of dry THF, 0.16 mL of 2-methoxyethanol and 1 mmol of naphthalene potassium at 25° C. for 2 days, and further polymerized together with 32 mmol, 31 mL, of 3,6-dimethyl-1,4-dioxane-2,5-dione at 25° C. for 2 hours. Thereafter, the reaction was stopped with 20 mmol, 3.6 mL, of methacrylic acid anhydride. The product was sedimented again in 600 mL of cold isopropanol to purify, and precipitated by centrifugation to collect the product. This product was dissolved in 100 mL of benzene, and lyophilized to collect 2.5 g of a copolymer. The 2.5 g copolymer obtained was dissolved in 1000 mL of water, and the solution was kept at 80° C. in an oil bath, and heated for 6 hours while stirring. After heating, the reaction mixture was allowed to stand overnight to collect a micelle solution. After 30 minutes, 10000 mL of the resulting micelle solution was thermally polymerized for 20 hours while keeping at 60° C. This solution was collected, and concentrated using an ultrafiltration membrane to a given concentration, to obtain a polymerized polymer micelle represented by the formula (2):

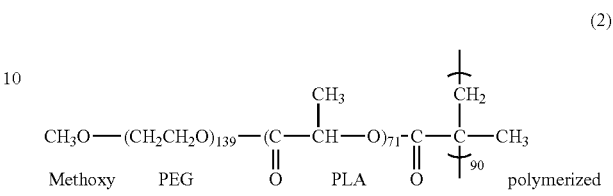

(molecular weight obtained by gel permeation chromatography being PEO/PLA=6100/4000).

Preparation of Electrophoretic Buffer

A 100 mg/ml polymerized polymer micelle (prepared with ultrapure water, pH 2.94) represented by the formula (2) was used by adjusting its pH to 8.8 with a 0.1 N sodium hydroxide.

The electrophoresis in the present examples was carried out using the Hitachi Microchip electrophoresis apparatus {cosmo-i (SV1100)}. As an electrophoretic buffer, a 10 mg/ml polymerized polymer micelle (pH 8.8) represented by the formula (2) was used (hereinafter referred to as polymer micelle). As a control electrophoretic buffer, 0.7% hydroxypropylmethyl cellulose was used (hereinafter referred to as conventional polymer).

As an electrophoresis method, electrophoresis was carried out using the following three kinds of methods:

Usual Method

A loading channel and a separation channel are charged with an electrophoretic buffer, and a sample reservoir is filled with 10 µl of a sample. While voltage is applied to the loading channel in which a remaining reservoir is filled with the electrophoretic buffer for 10µl, 300 V, 60 seconds, the sample in the sample reservoir is loaded on the loading channel. Subsequently, 890 V of the separation voltage is loaded for 180 seconds while applying 130 V of squeezing voltage to the separation channel;

PP Method

A loading channel and a separation channel are charged with an electrophoretic buffer, and 2 µl of a sample is loaded to a sample reservoir. The sample is introduced into a loading channel, more specifically into an intersection portion of the loading channel and the separation channel by loading a pressure of from 1 to 5.5 kPa for 1 second to the sample reservoir in the state that the electrophoretic buffer is not filled into a reservoir other than an outlet on a detection side. Subsequently, a pressure of from 1 to 7 kPa for 1 second is applied to the separation channel from a side opposite to an outlet of the separation channel, to migrate the sample downstream of the separation channel; and Improved PP Method In the above-mentioned PP method, a pressure when introducing a sample into the loading channel is from 5.5 to 7 kPa for 1 second, and a pressure applied to the separation channel is from 1 to 10 kPa for 1 second. Alternatively, a pressure when introducing a sample into the loading channel is from 1 to 5.5 kPa for 1 second, and a pressure applied to the separation channel is 7 to 10 kpa for 1 second. Here, in the PP method, the sample is introduced into the intersection portion of the loading channel and the separation channel in a proper amount, specifically 0.2 μl, while in the improved PP method, the sample is introduced in an excessive amount, specifically 0.5 μl.

Hereinafter, the pressure when injecting a sample into a loading channel (specifically, an intersection portion of a loading channel and a separation channel) is referred to as a former pressure, and a pressure for pressurizing a separation channel to migrate a sample at a crossing section to a downstream part (detection part side) of a separation channel is referred to as a latter pressure.

Strengths of the former pressure and the latter pressure in the PP method and its improved method used in the present Examples were:

L: 0.1 cm$^3$ air injection≈1 to 2 kPa,
LM: 0.2 to 0.4 cm$^3$ air injection≈2 to 3 kPa,
M: 0.5 cm$^3$ air injection≈3 to 3.5 kPa,
MH: 0.6 to 0.9 cm$^3$ air injection≈3.5 to 5.5 kPa,
H: 1 cm$^3$ air injection≈5.5 to 7 kPa,
HH: 1 to 1.5 cm$^3$ air injection≈7 to 10 kPa.

Example 1

Polymer Micelle+Usual Method

Using the polymer micelle as an electrophoretic buffer, separation of two DNA markers (100 bp and 800 bp) was carried out by electrophoresis in accordance with the usual method. As a result, a peak did not appear within the migration time of 180 seconds (FIG. 1).

Example 2

Polymer Micelle+PP Method

Figure 2:
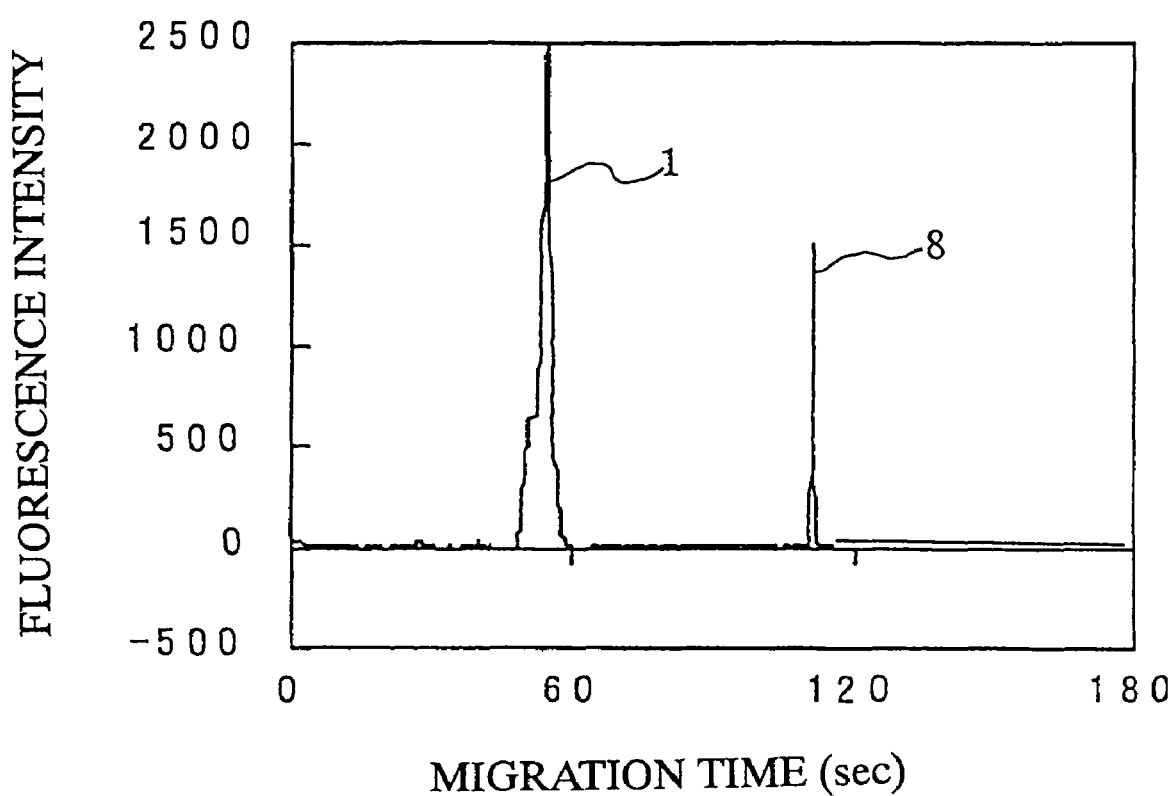
FIG. 2 is a diagram showing the results for studying electrophoretic conditions in a microchip electrophoresis.

Example 1 was carried out in accordance with the PP method. An intensity of the former P was M, and an intensity of the latter P was L. As a result, two peaks were found within the migration time of 180 seconds (FIG. 2).

Example 3

Polymer Micelle+PP Method

Figure 3:
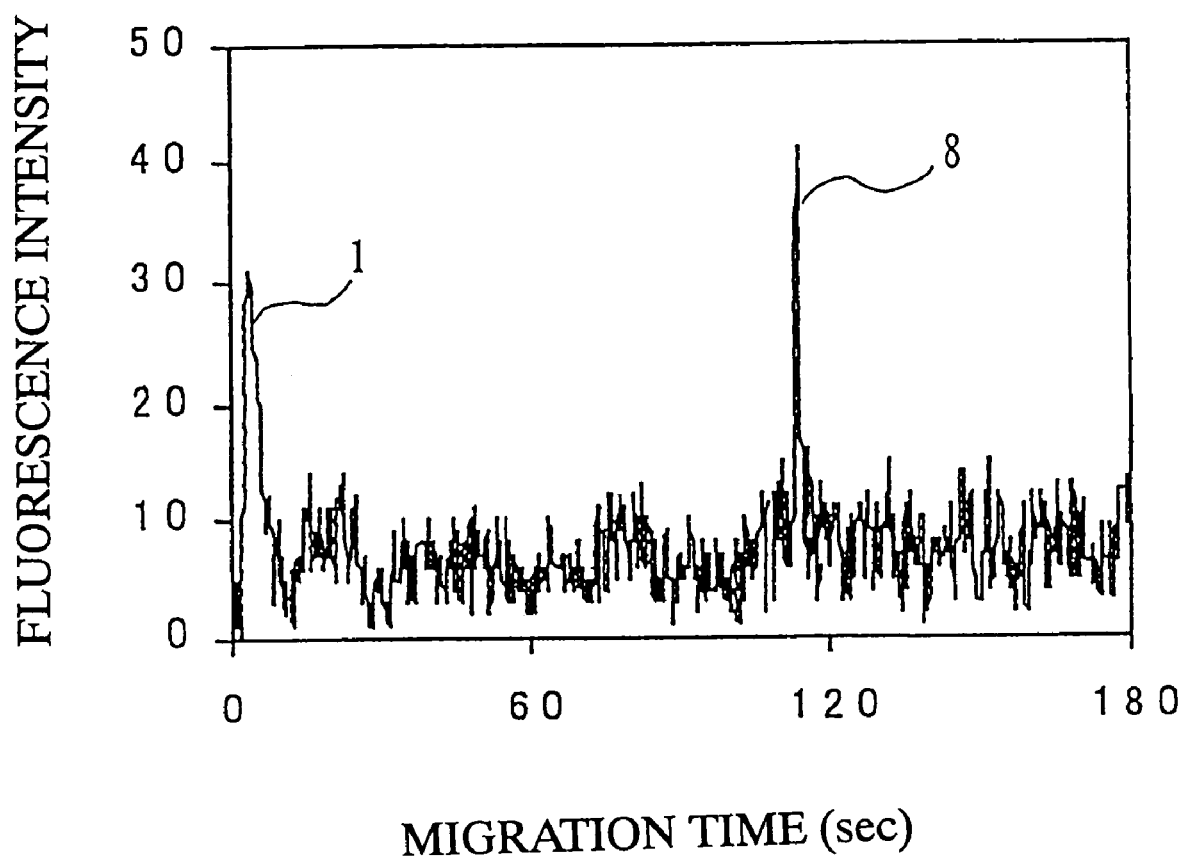
FIG. 3 is a diagram showing the results for studying electrophoretic conditions in a microchip electrophoresis.

An intensity of the former P of Example 2 was M, and an intensity of the latter P was M. As a result, the migration time of 100 bp was accelerated (FIG. 3).

Example 4

Polymer Micelle+PP Method

Figure 4:
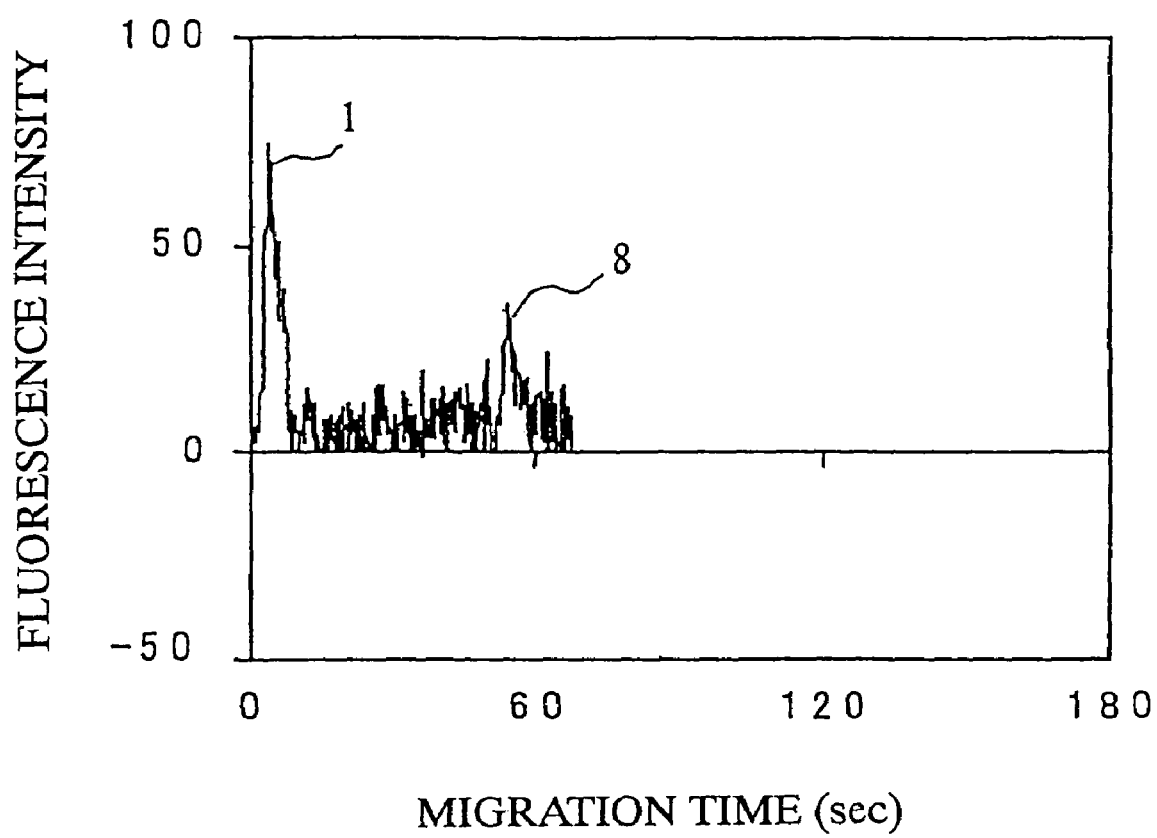
FIG. 4 is a diagram showing the results for studying electrophoretic conditions in a microchip electrophoresis.

An intensity of the former P of Example 2 was M, and an intensity of the latter P was H. As a result, the migration time was shortened (FIG. 4).

Example 5

Polymer Micelle+Usual Method

Figure 5:
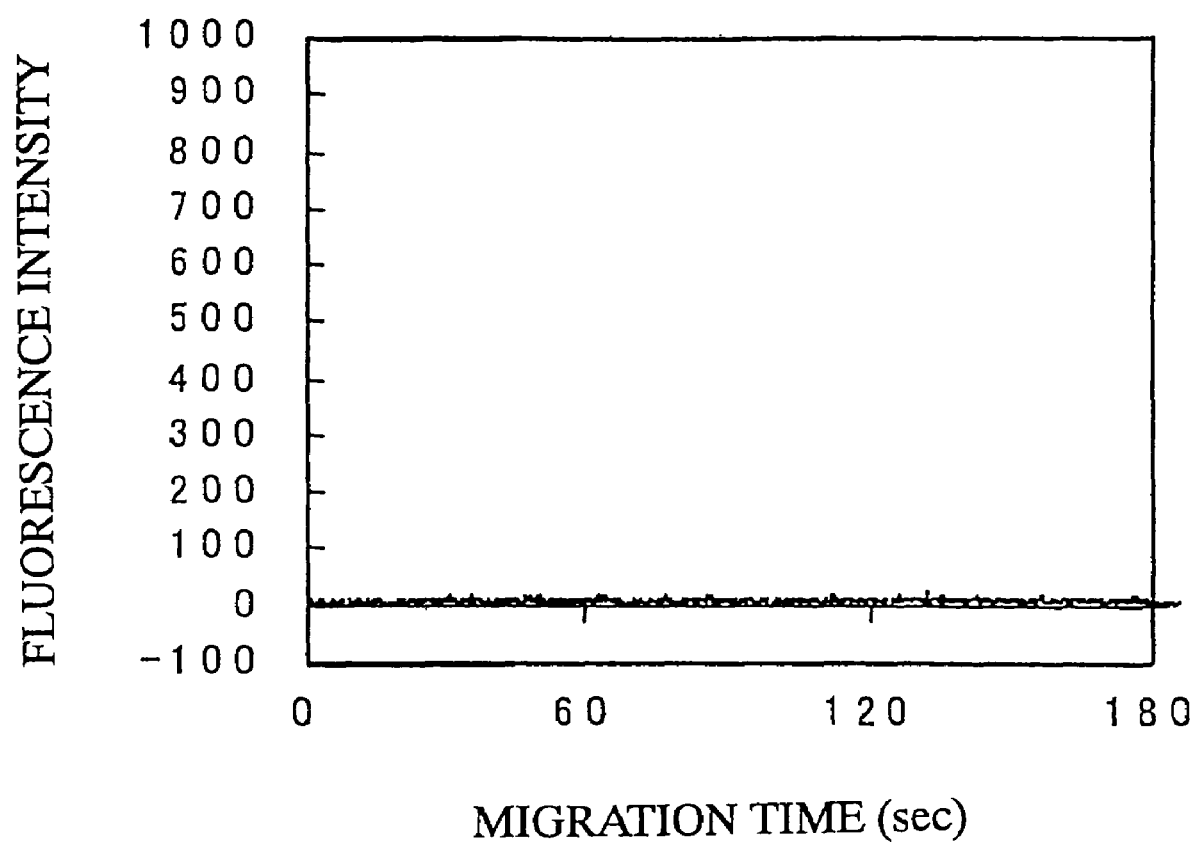
FIG. 5 is a diagram showing the results for studying electrophoretic conditions in a microchip electrophoresis.

Using the polymer micelle as an electrophoretic buffer, separation of three DNAs (100 bp, 500 bp, and 800 bp) was carried out in accordance with the usual method. As a result, the peak did not appear within the migration time of 180 seconds (FIG. 5).

Example 6

Polymer Micelle+PP Method

Figure 6:
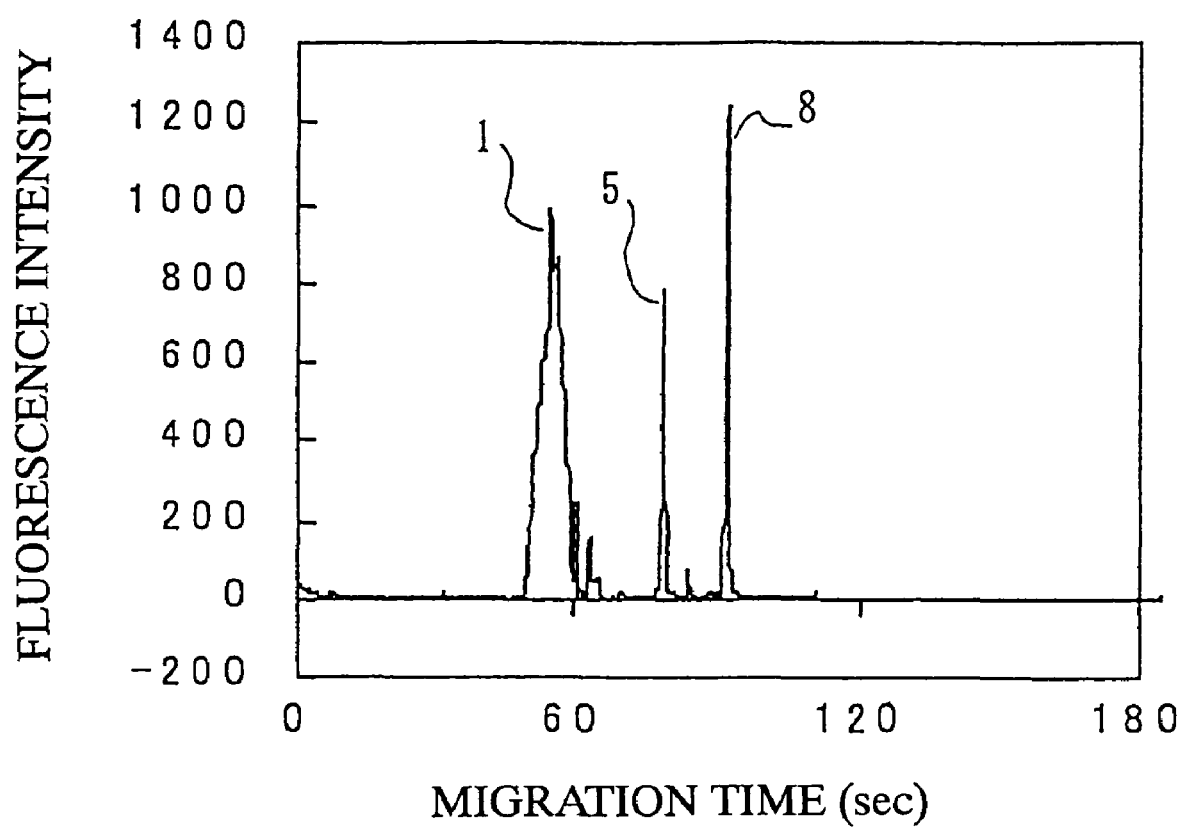
FIG. 6 is a diagram showing the results for studying electrophoretic conditions in a microchip electrophoresis.

Example 5 was carried out in accordance with the PP method. An intensity of the former P was L, and an intensity of the latter P was LM. As a result, three peaks were found within the migration time of 120 seconds (FIG. 6).

Example 7

Polymer Micelle+PP Method

Figure 7:
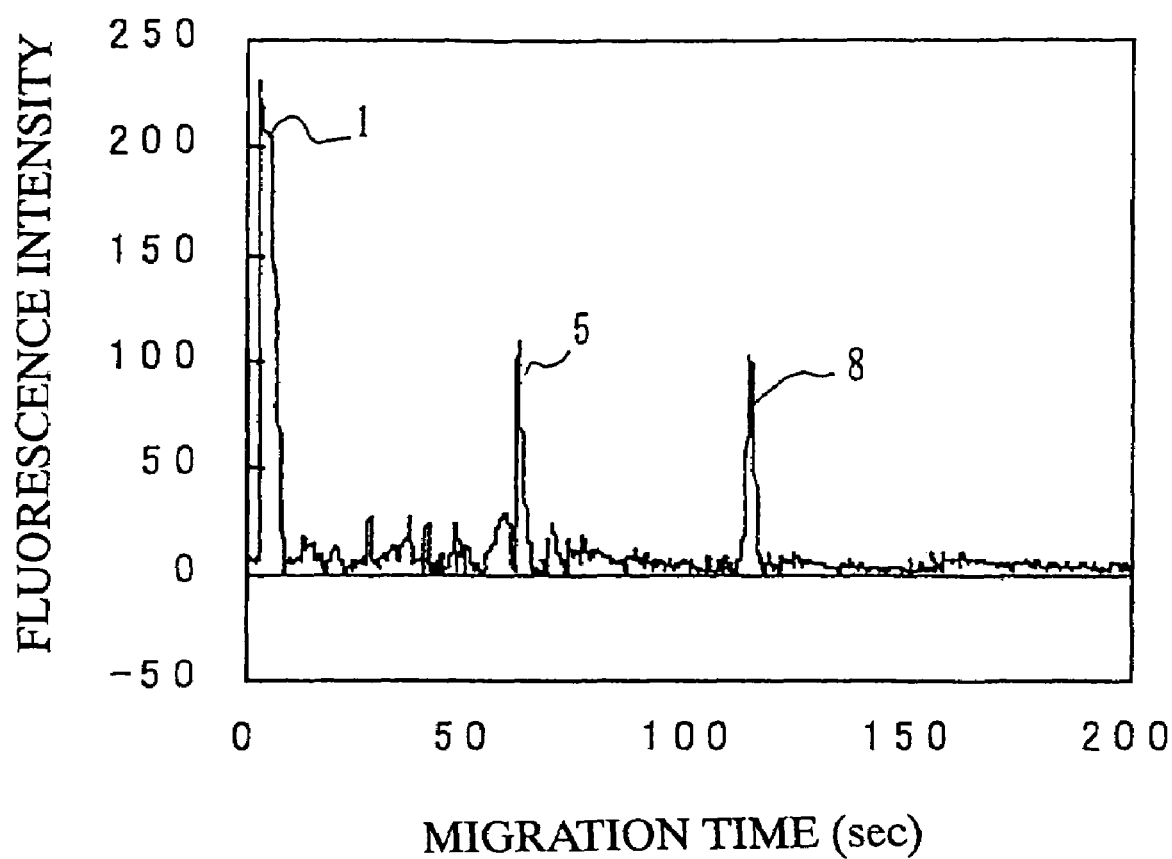
FIG. 7 is a diagram showing the results for studying electrophoretic conditions in a microchip electrophoresis.

Example 5 was carried out in accordance with the PP method. An intensity of the former P was L, and an intensity of the latter P was M. As a result, the migration time for 100 bp and 500 bp was accelerated (FIG. 7).

Example 8

Polymer Micelle+PP Method

Figure 8:
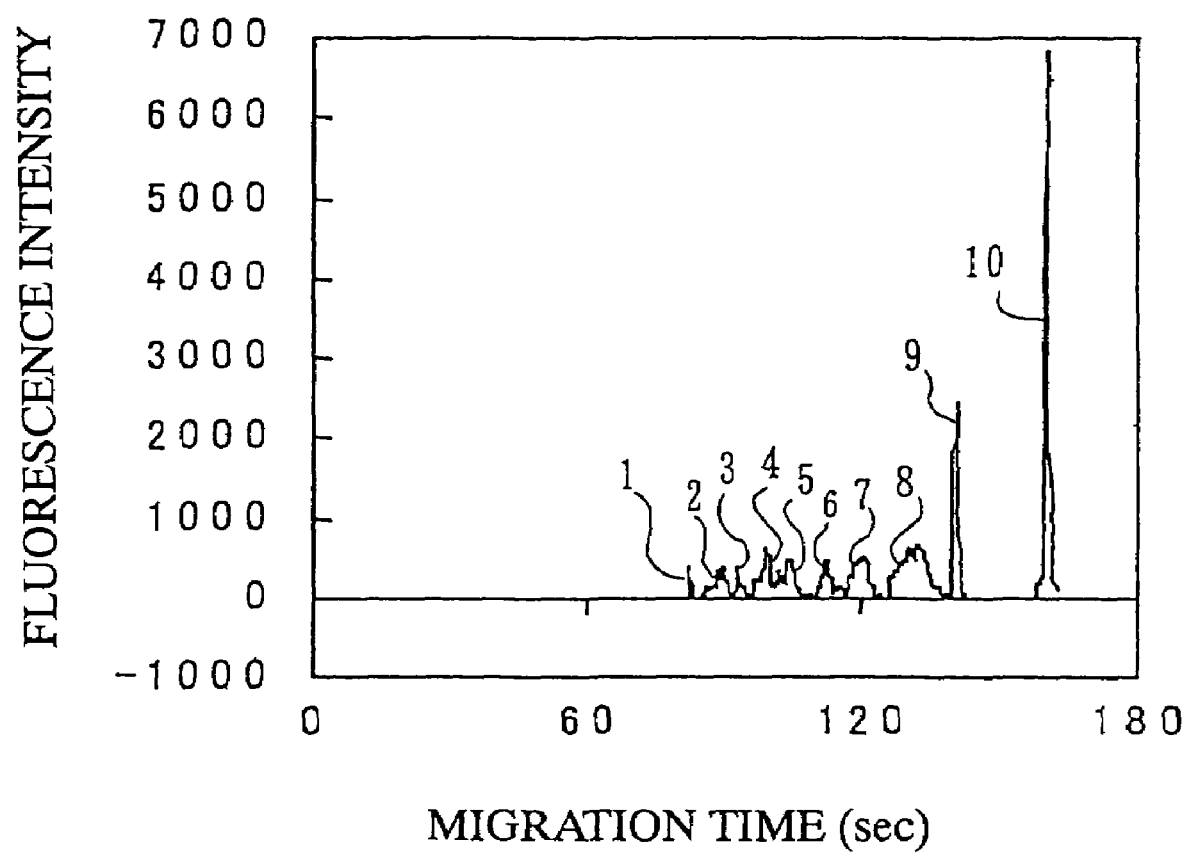
FIG. 8 is a diagram showing the results for studying electrophoretic conditions in a microchip electrophoresis.

Using the polymer micelle as an electrophoretic buffer, separation of ten DNAs (100 bp to 1000 bp) was carried out in accordance with the PP method. An intensity of the former P was M, and an intensity of the latter P was L. As a result, 10 peaks were found within the migration time of 180 seconds (FIG. 8).

Example 9

Polymer Micelle+PP Method

Figure 9:
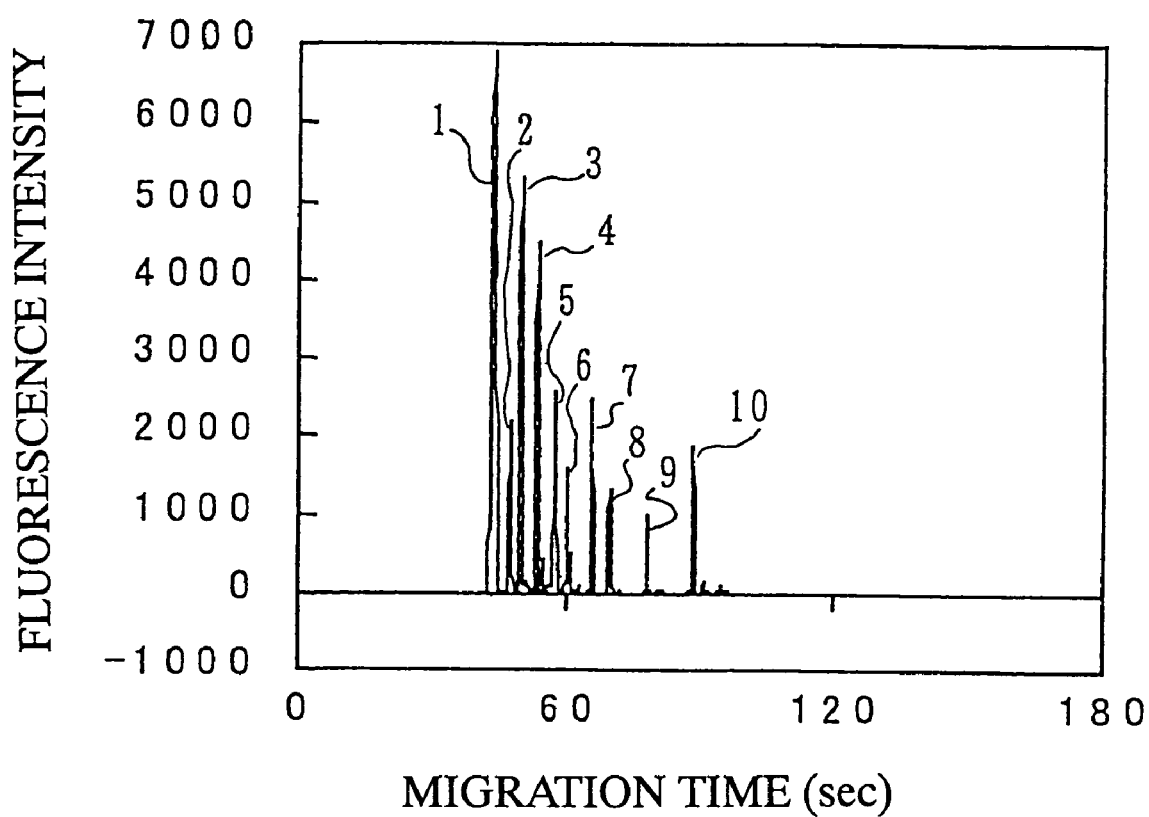
FIG. 9 is a diagram showing the results for studying electrophoretic conditions in a microchip electrophoresis.

Example 8 was carried out in accordance with the PP method. An intensity of the former P was M, and an intensity of the latter P was LM. As a result, 10 peaks were found within the migration time of 90 seconds (FIG. 9).

Example 10

Polymer Micelle+PP Method

Figure 10:
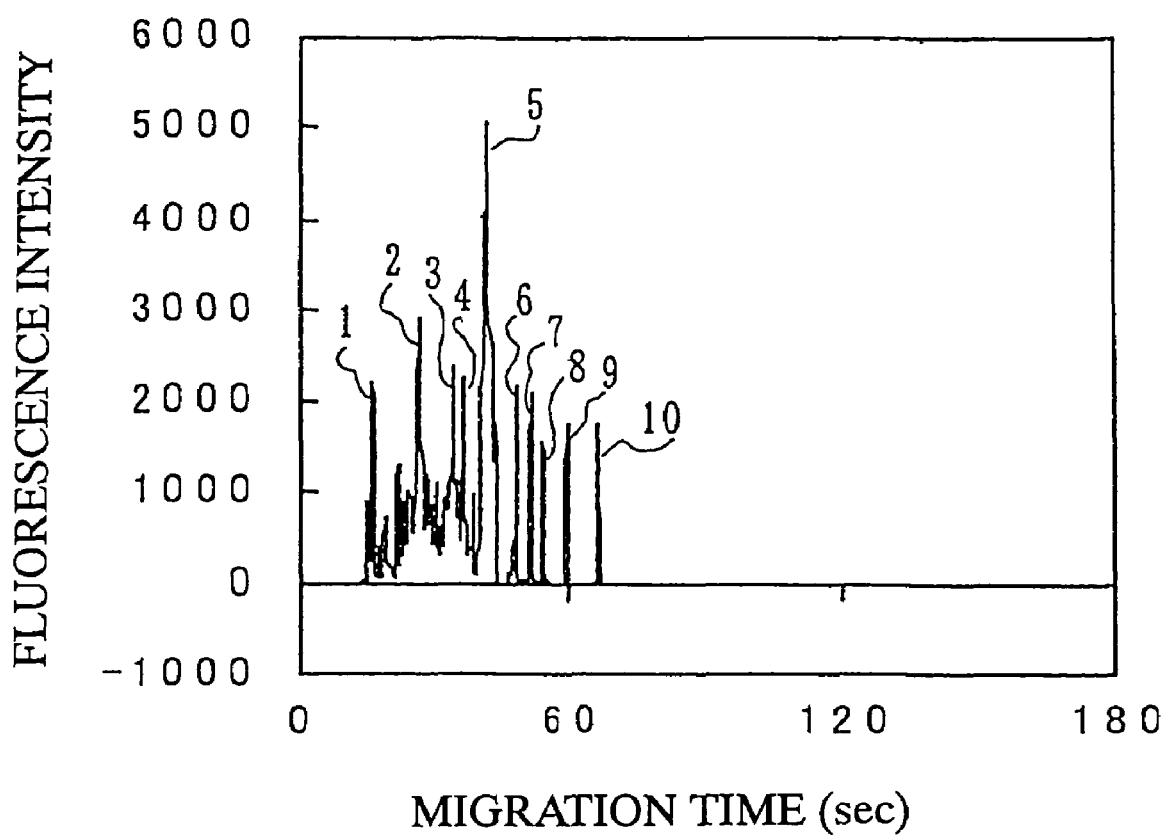
FIG. 10 is a diagram showing the results for studying electrophoretic conditions in a microchip electrophoresis.

Example 8 was carried out in accordance with the PP method. An intensity of the former P was M, and an intensity of the latter P was H. As a result, 10 peaks were found within the migration time of about 60 seconds (FIG. 10).

Example 11

Polymer Micelle+Improved PP Method

Figure 11:
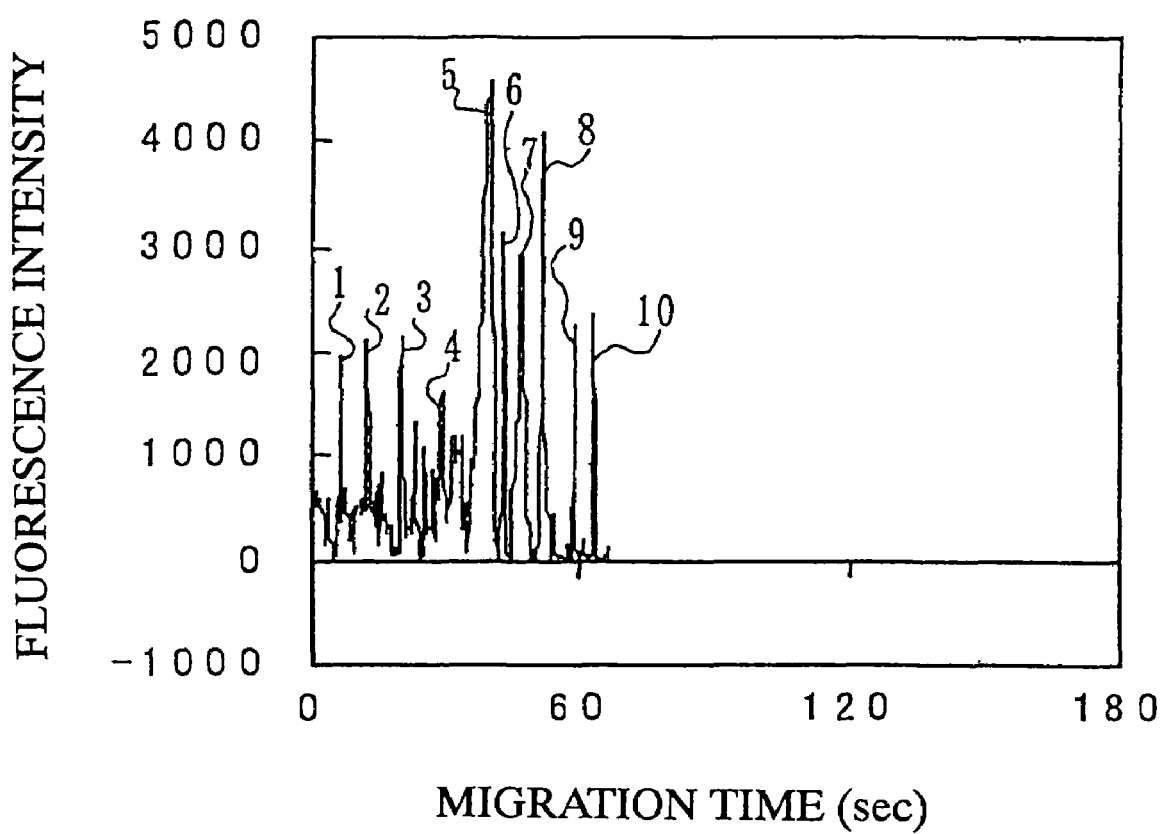
FIG. 11 is a diagram showing the results for studying electrophoretic conditions in a microchip electrophoresis.

Example 8 was carried out in accordance with the PP method. An intensity of the former P was M, and an intensity of the latter P was HH. As a result, 10 peaks were similarly found within the migration time of 60 seconds, and the migration time was accelerated (FIG. 11).

Example 12

Polymer Micelle+PP Method

Figure 12:
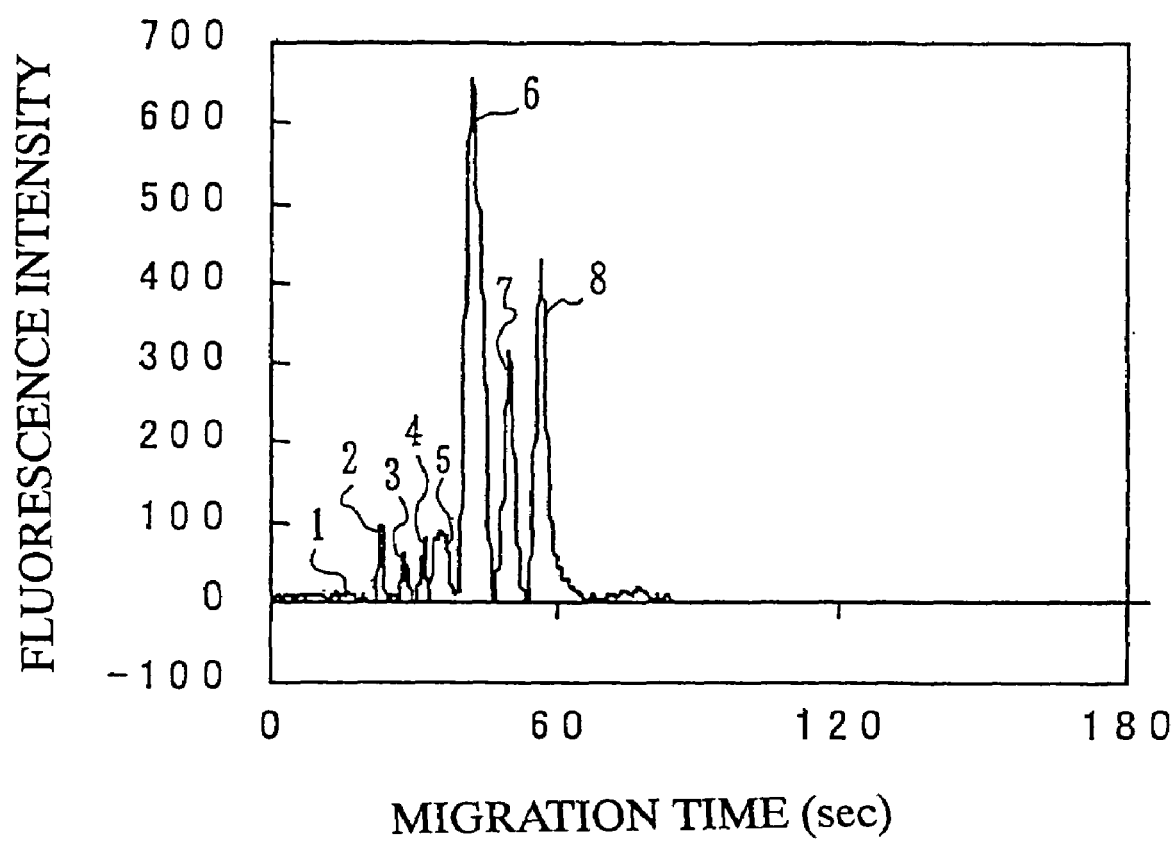
FIG. 12 is a diagram showing the results for studying electrophoretic conditions in a microchip electrophoresis.

Using the polymer micelle as an electrophoretic buffer, separation of eight DNAs (100 to 800 bp) was carried out in accordance with the PP method. An intensity of the former P was M, and an intensity of the latter P was MH (FIG. 12).

About 8 peaks were found within 60 seconds.

Example 13

Polymer Micelle+PP Method

Figure 13:
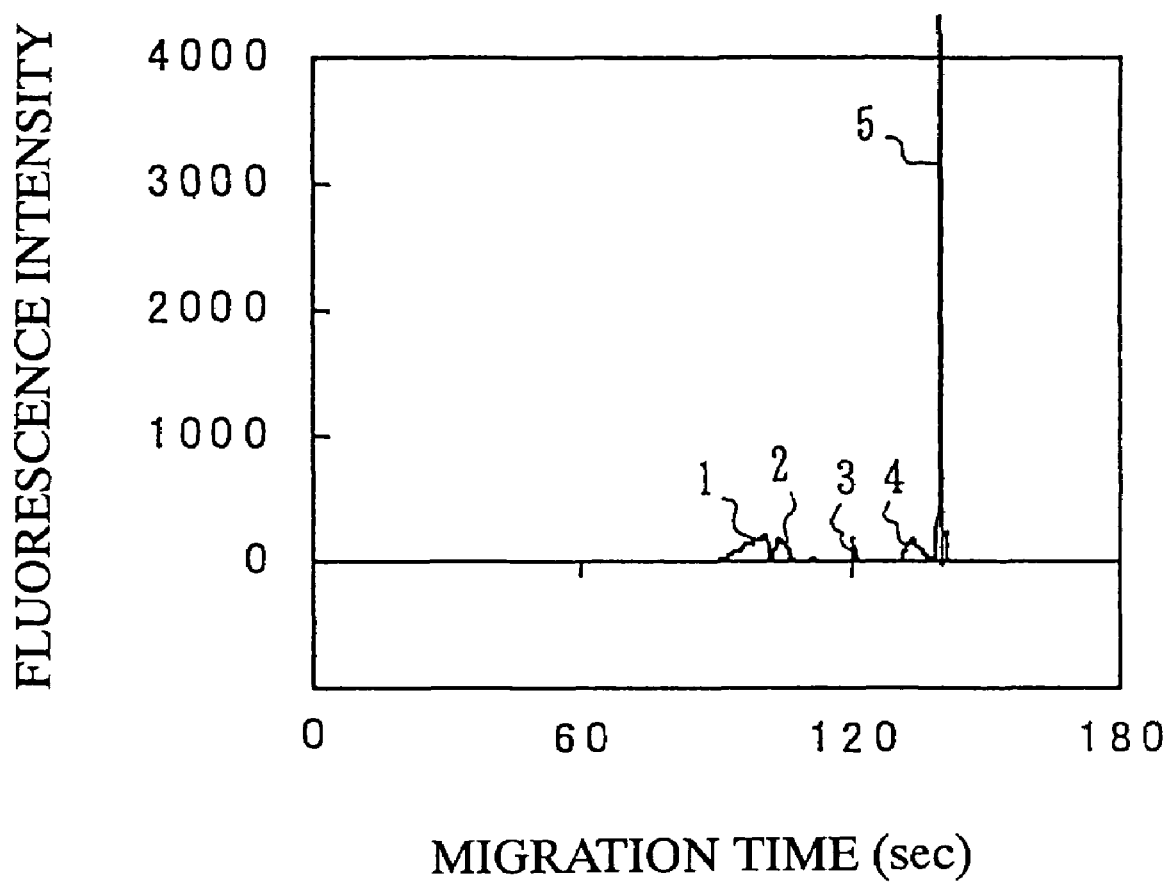
FIG. 13 is a diagram showing the results for studying electrophoretic conditions in a microchip electrophoresis.

Using the polymer micelle as an electrophoretic buffer, separation of fifteen DNAs (1 to 15 bp (5 kbp: high)) was carried out in accordance with the PP method. P of the former was M, and that of the latter was L (FIG. 13). As a result, 5 peaks were found within 180 seconds.

Example 14

Polymer Micelle+PP Method

Figure 14:
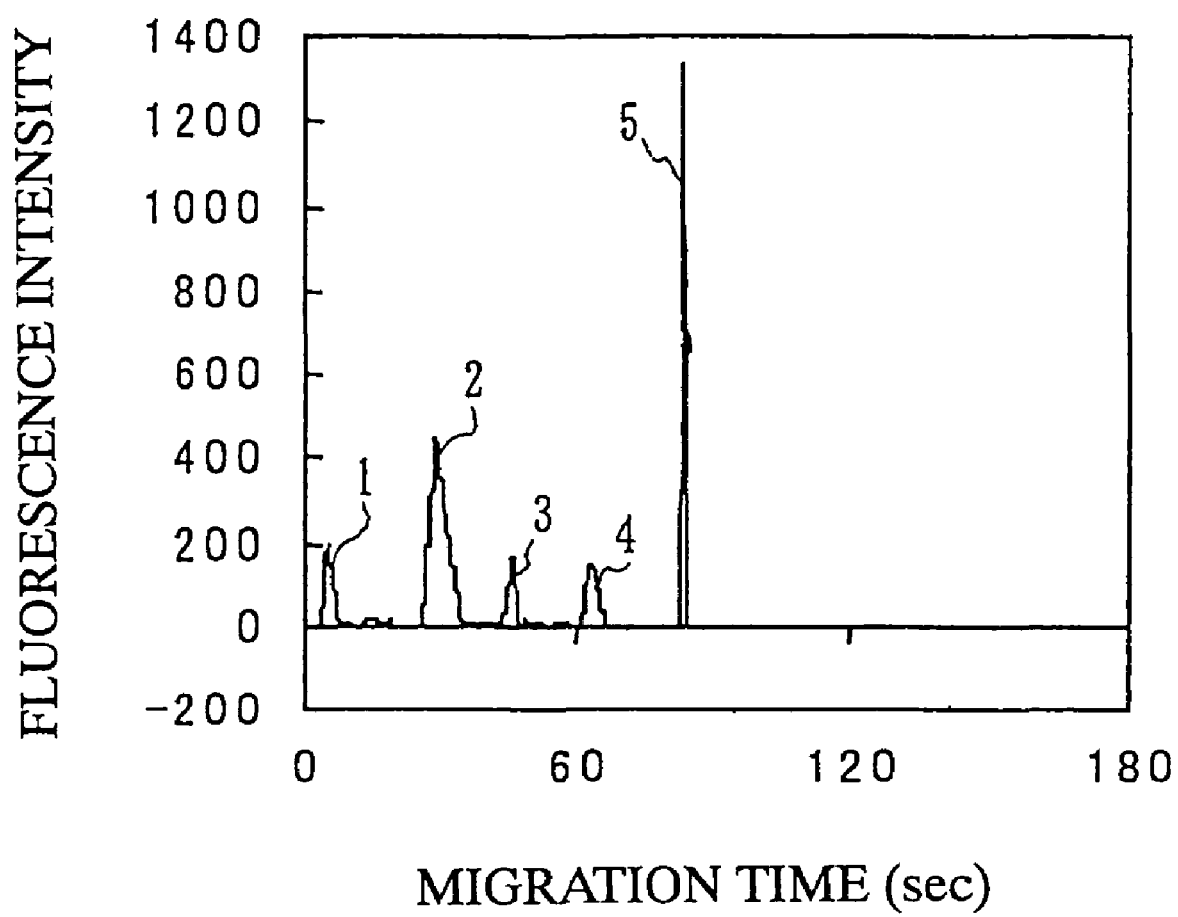
FIG. 14 is a diagram showing the results for studying electrophoretic conditions in a microchip electrophoresis.

Example 13 was carried out in accordance with the PP method. The former was M, and the latter was M. As a result, the migration time was shortened (FIG. 14).

Example 15

Polymer Micelle+PP Method

Figure 15:
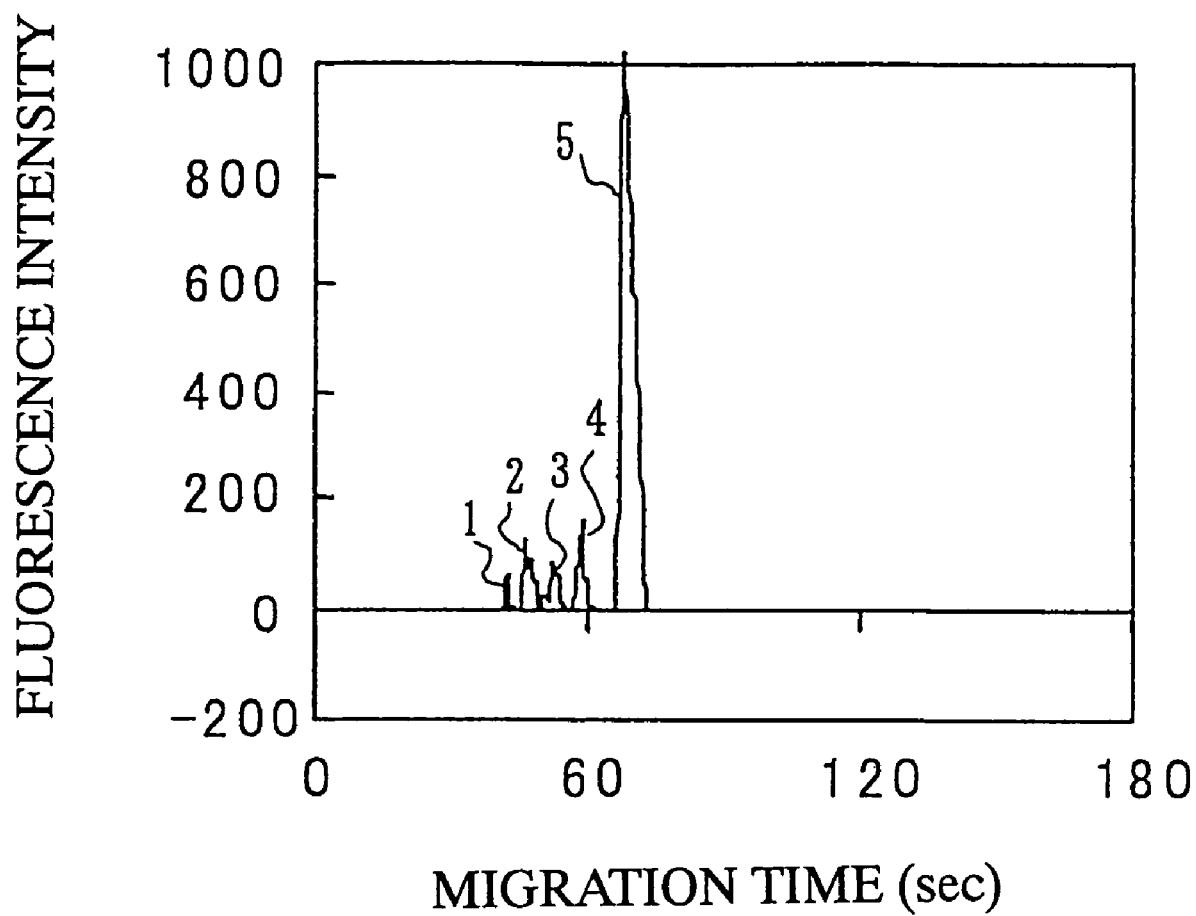
FIG. 15 is a diagram showing the results for studying electrophoretic conditions in a microchip electrophoresis.

Example 13 was carried out in accordance with the PP method. The former was M, and the latter was H. As a result, the migration interval was shortened (FIG. 15).

Example 16

Polymer Micelle+Improved PP Method

Figure 16:
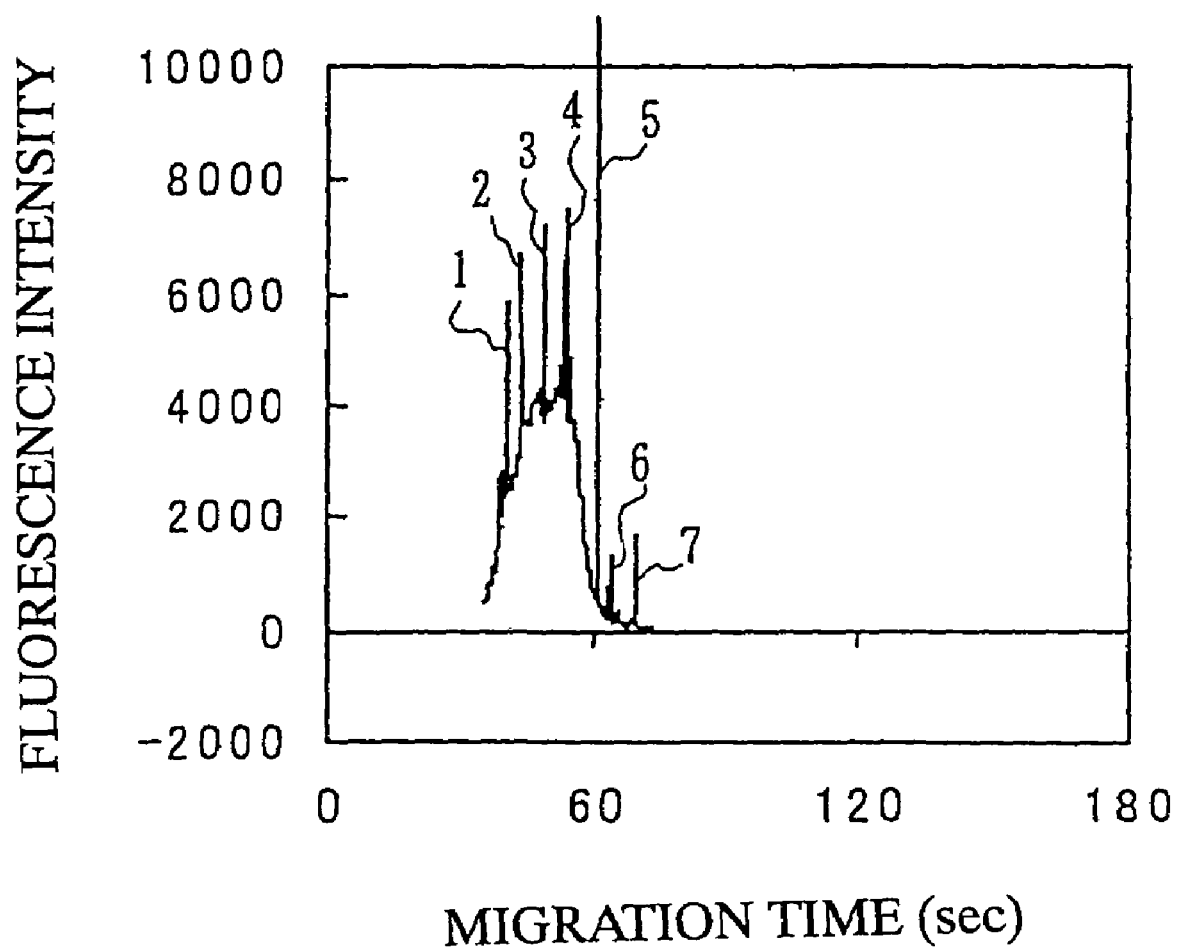
FIG. 16 is a diagram showing the results for studying electrophoretic conditions in a microchip electrophoresis.

Example 13 was carried out in accordance with the PP method. The former was M, and the latter was HH. As a result, it was possible to further detect up to 7 kbp DNA (FIG. 16).

Example 17

Polymer Micelle+Improved PP Method

Figure 17:
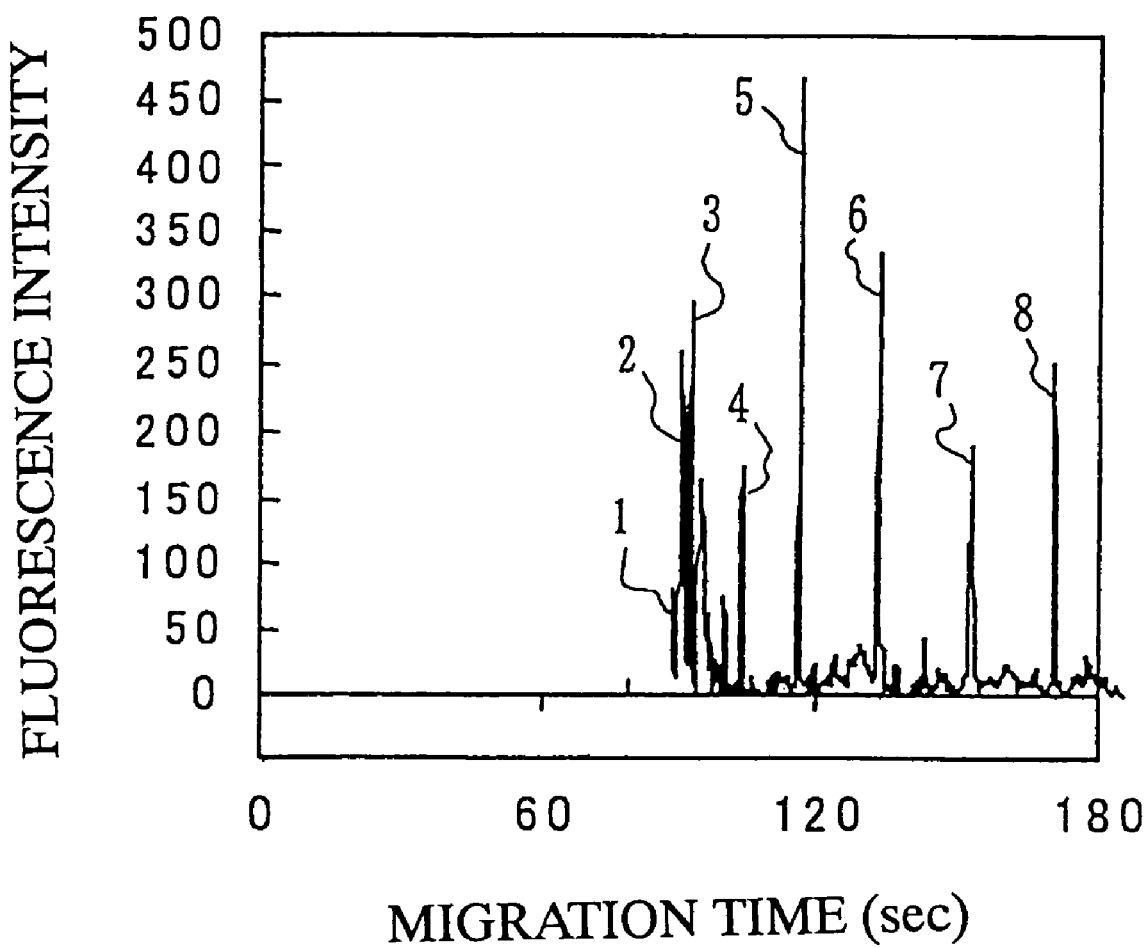
FIG. 17 is a diagram showing the results for studying electrophoretic conditions in a microchip electrophoresis.

Example 13 was carried out in accordance with the PP method. The former was H, and the latter was L. As a result, 8 peaks were found within 180 seconds (FIG. 17).

Example 18

Polymer Micelle+Improved PP Method

Figure 18:
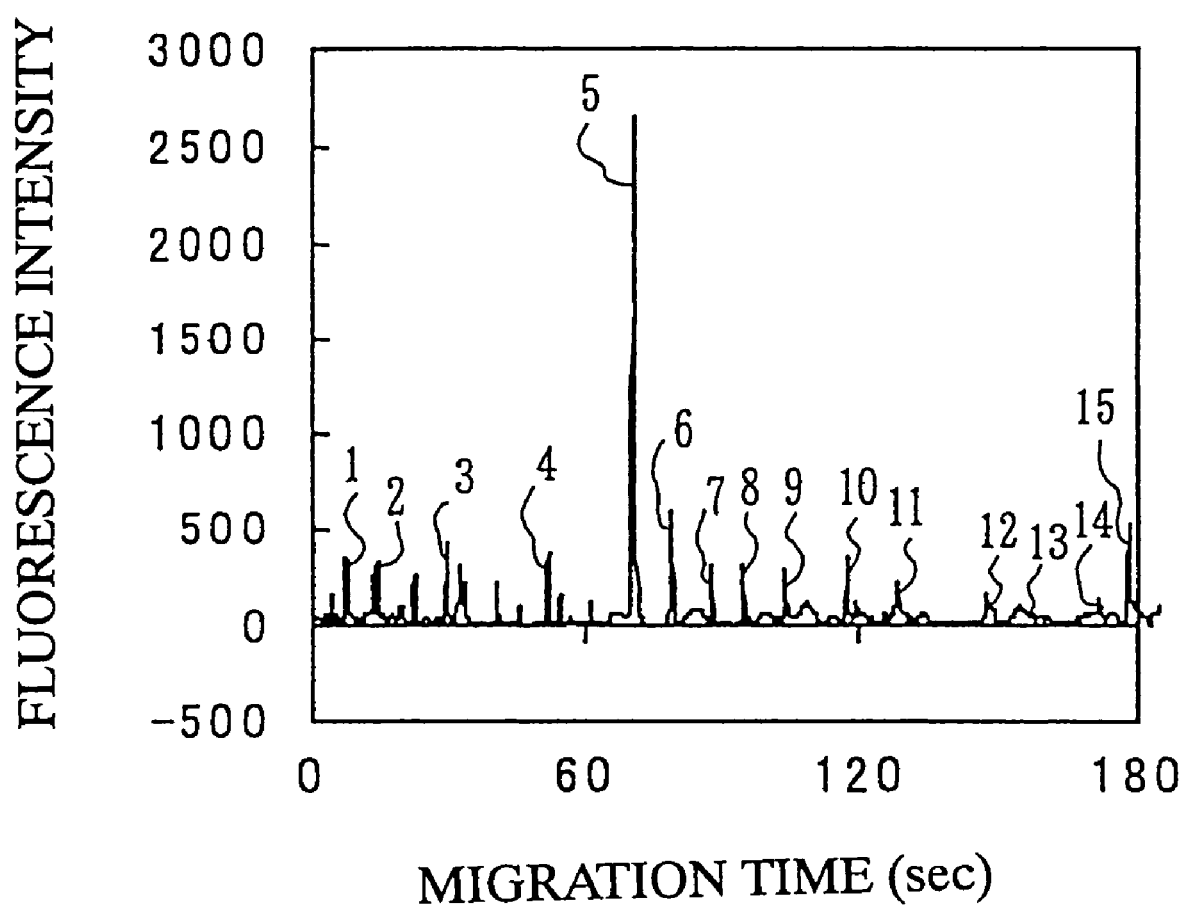
FIG. 18 is a diagram showing the results for studying electrophoretic conditions in a microchip electrophoresis.

Example 13 was carried out in accordance with the PP method. The former was H, and the latter was M. As a result, 15 peaks were detected within 180 seconds (FIG. 18).

Example 19

Polymer Micelle+Improved PP Method

Figure 19:
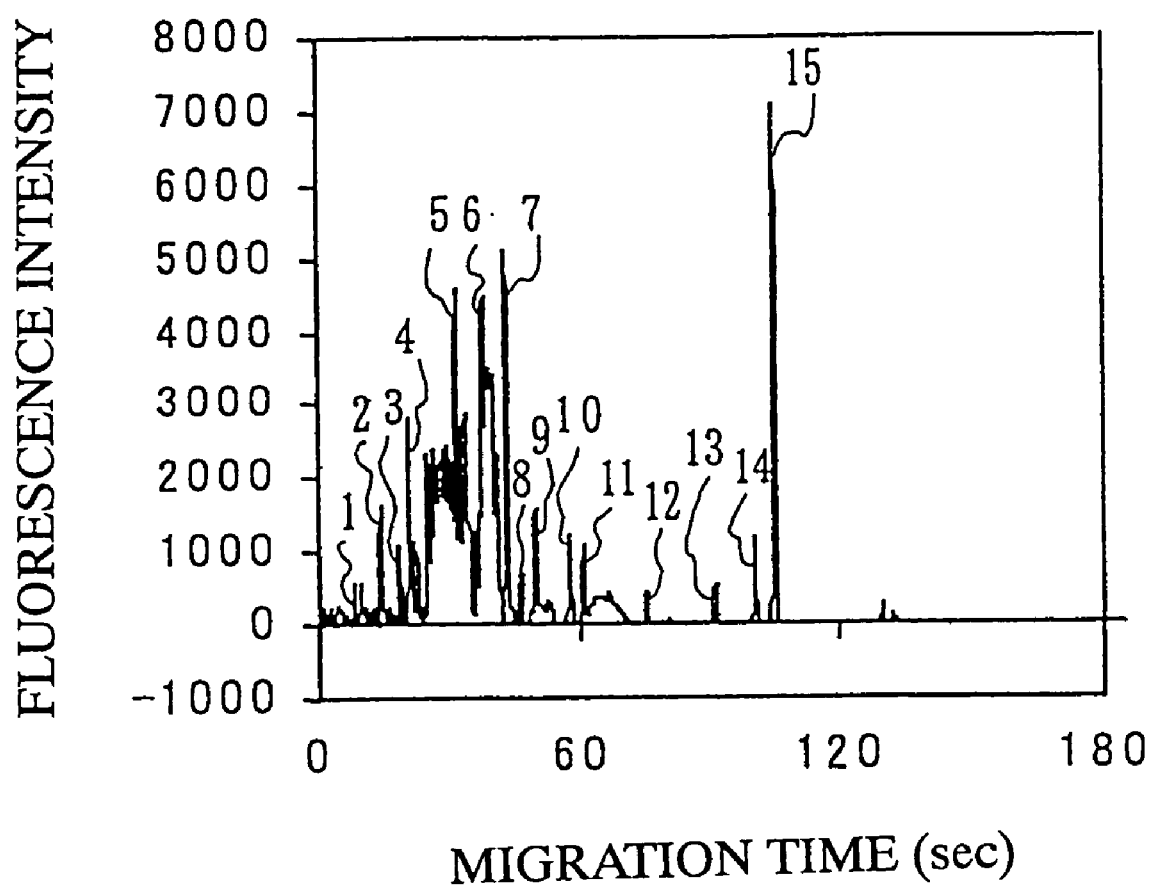
FIG. 19 is a diagram showing the results for studying electrophoretic conditions in a microchip electrophoresis.

Example 13 was carried out in accordance with the PP method. The former was H, and the latter was H. As a result, 15 peaks were found within 100 seconds (FIG. 19).

Example 20

Background

Figure 20:
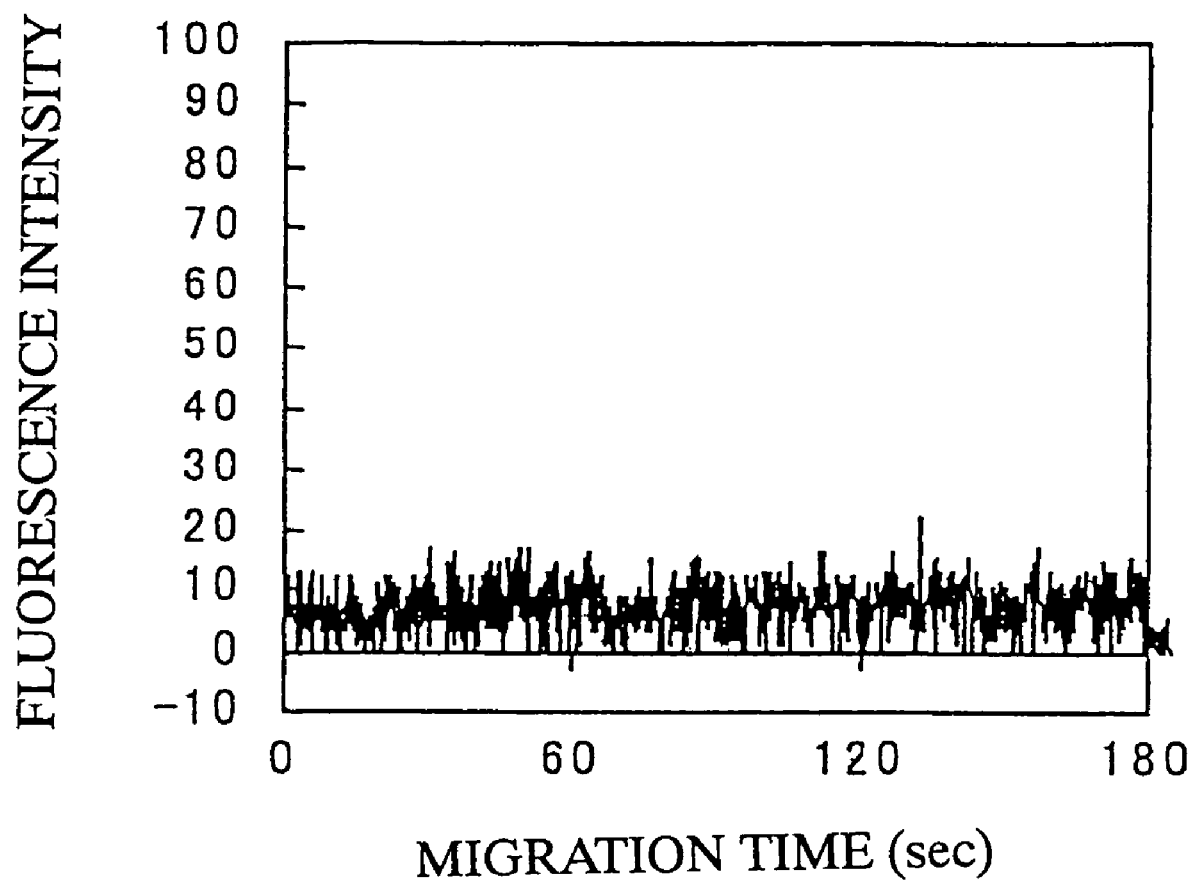
FIG. 20 is a diagram showing the results for studying electrophoretic conditions in a microchip electrophoresis.

In this electrophoresis, background was examined for only a polymer micelle buffer and a fluorescent reagent without DNA. As a result, since a peak ascribed to the polymer micelle was not detected, it was thought that a series of detected peaks were peaks of each of the DNAs when the present polymer micelle was used as an electrophoretic buffer (FIG. 20).

The effectiveness of the present polymer micelle was examined by comparing between one in which the PP method was applied to the conventional electrophoretic buffer and one in which the PP method was applied to an electrophoretic buffer using the polymer micelle. The comparison was carried out to the case where the conventional polymer (0.7% HPMC (hydroxypropylmethyl cellulose)) was used as an electrophoretic buffer.

Example 21

Conventional Polymer+Usual Method

Figure 21:
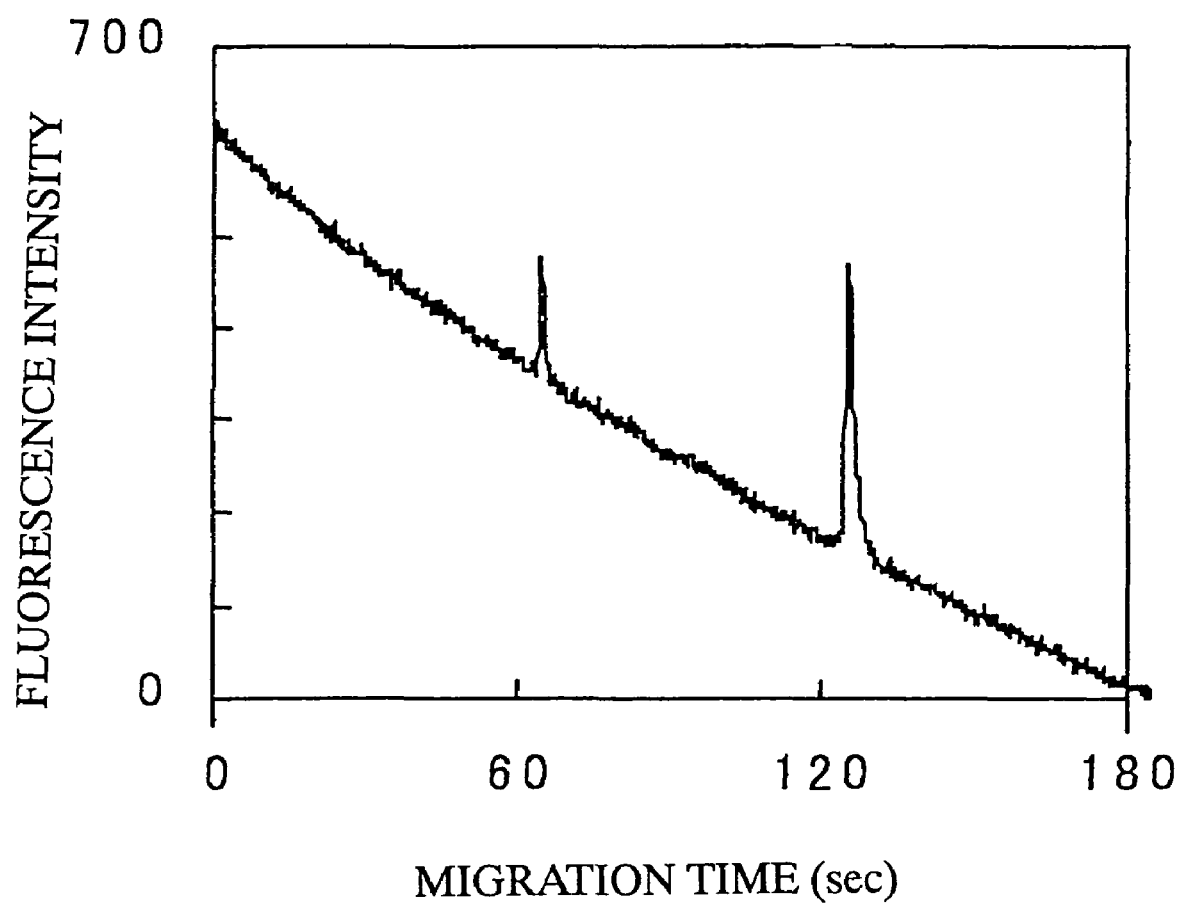
FIG. 21 is a diagram showing the results for studying electrophoretic conditions in a microchip electrophoresis.

Separation of two DNA markers (100 bp and 800 bp) was carried out using the conventional polymer solution (0.7% HPMC (hydroxypropylmethyl cellulose)) as an electrophoretic buffer in accordance with the usual method (FIG. 21).

Example 22

Conventional Polymer+PP Method

Figure 22:
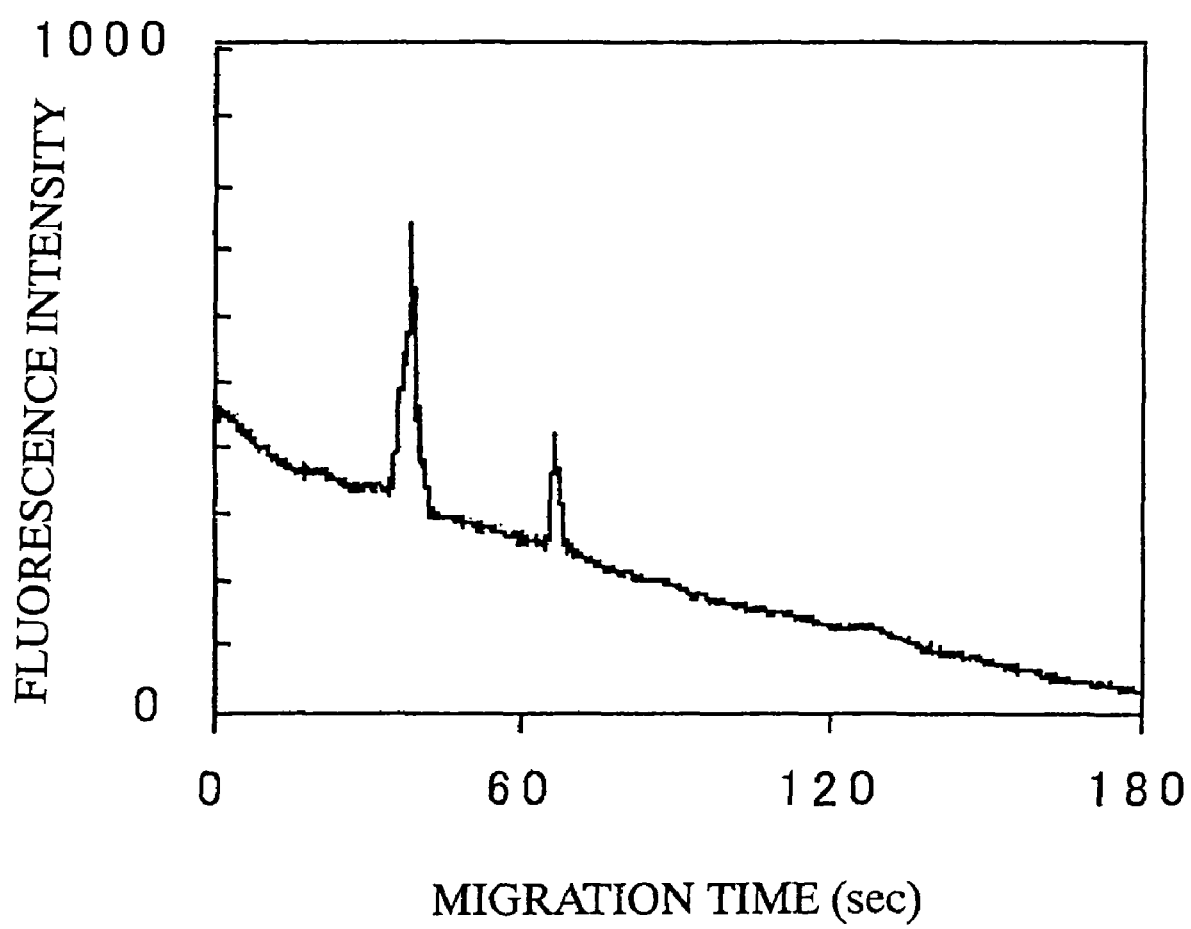
FIG. 22 is a diagram showing the results for studying electrophoretic conditions in a microchip electrophoresis.

Example 21 was carried out by an electrophoresis method of the earlier application. The former was M, and P of the latter was LM. As a result, the shortening of the migration time was shown (FIG. 22).

Example 23

Conventional Polymer+PP Method

Figure 23:
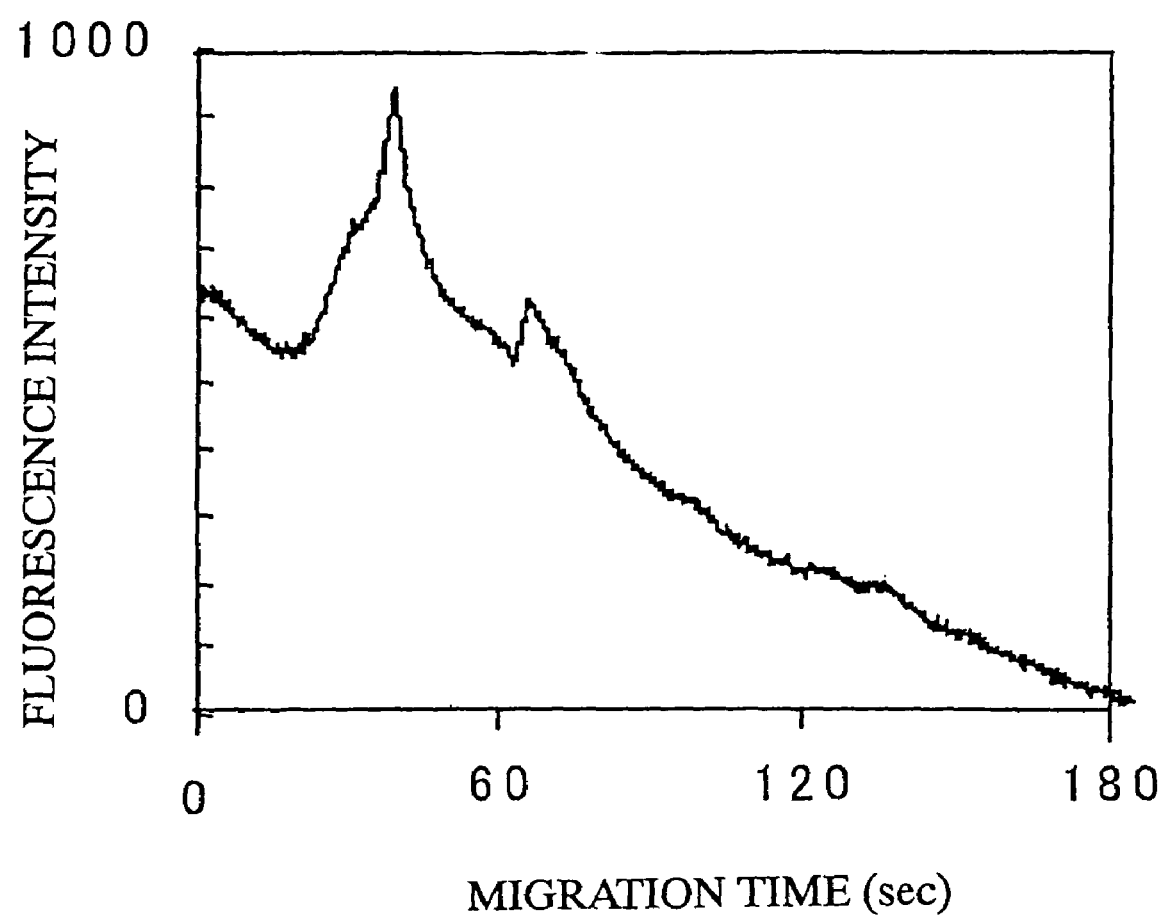
FIG. 23 is a diagram showing the results for studying electrophoretic conditions in a microchip electrophoresis.

In Example 22, the former was M, and P of the latter was MH. As a result, the peak became broad (FIG. 23).

Example 24

Conventional Polymer+Usual Method

Figure 24:
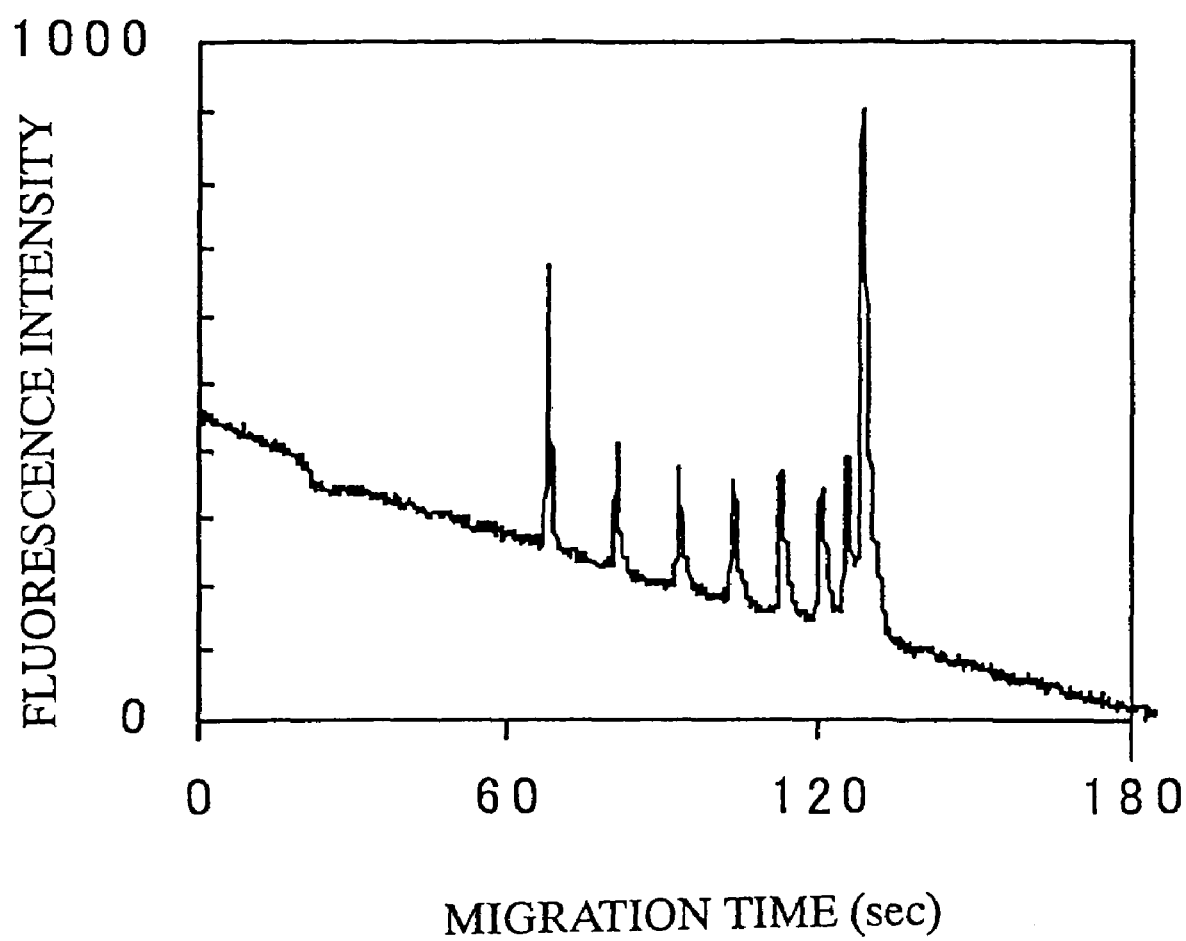
FIG. 24 is a diagram showing the results for studying electrophoretic conditions in a microchip electrophoresis.

Separation of eight DNA markers (100 bp to 800 bp) was carried out using the conventional polymer solution (0.7% HPMC (hydroxypropylmethyl cellulose)) as an electrophoretic buffer in accordance with the usual method (FIG. 24).

Example 25

Conventional Polymer+PP Method

Figure 25:
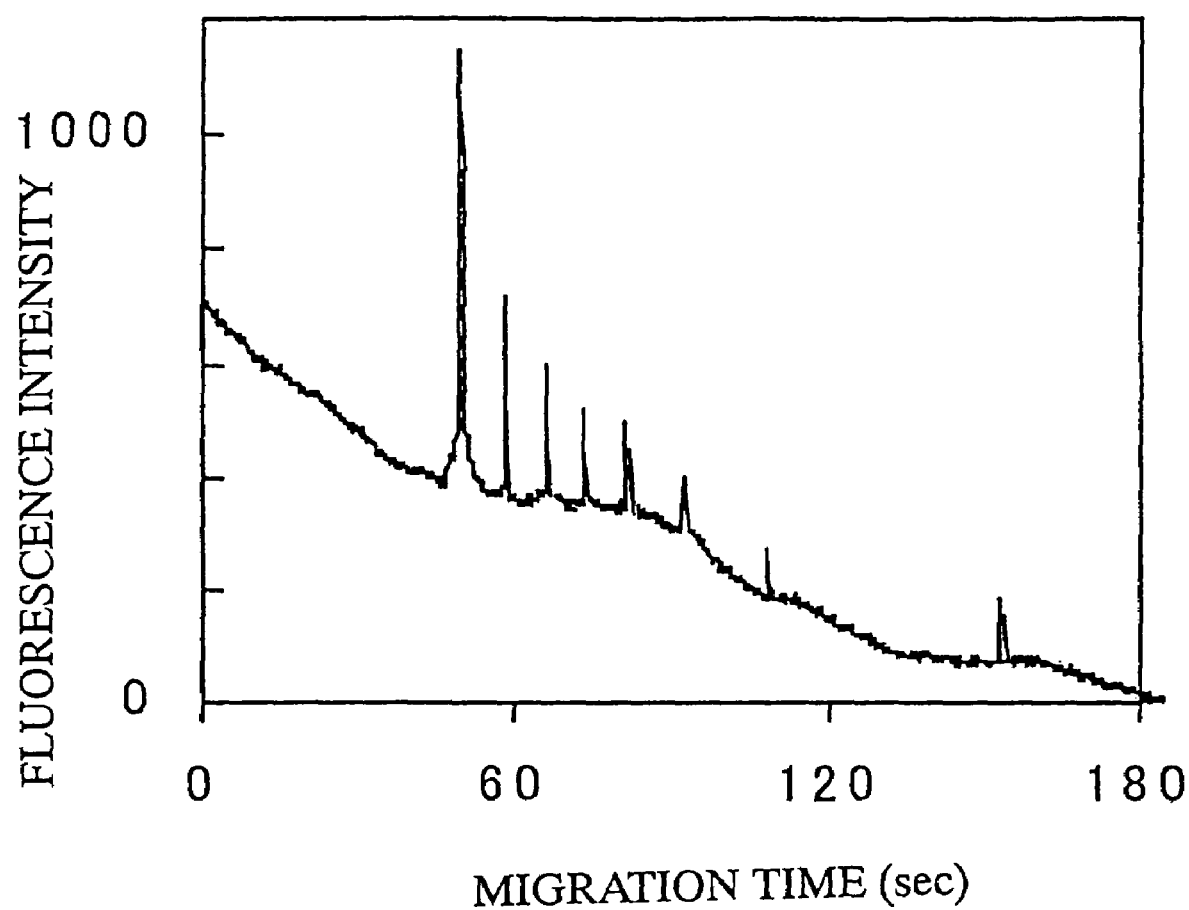
FIG. 25 is a diagram showing the results for studying electrophoretic conditions in a microchip electrophoresis.

Example 24 was carried out in accordance with the PP method. The former was M, and P of the latter was LM. As a result, the peak of the former was accelerated, but the peak interval was widened (FIG. 25).

Example 26

Conventional Polymer+PP Method

Figure 26:
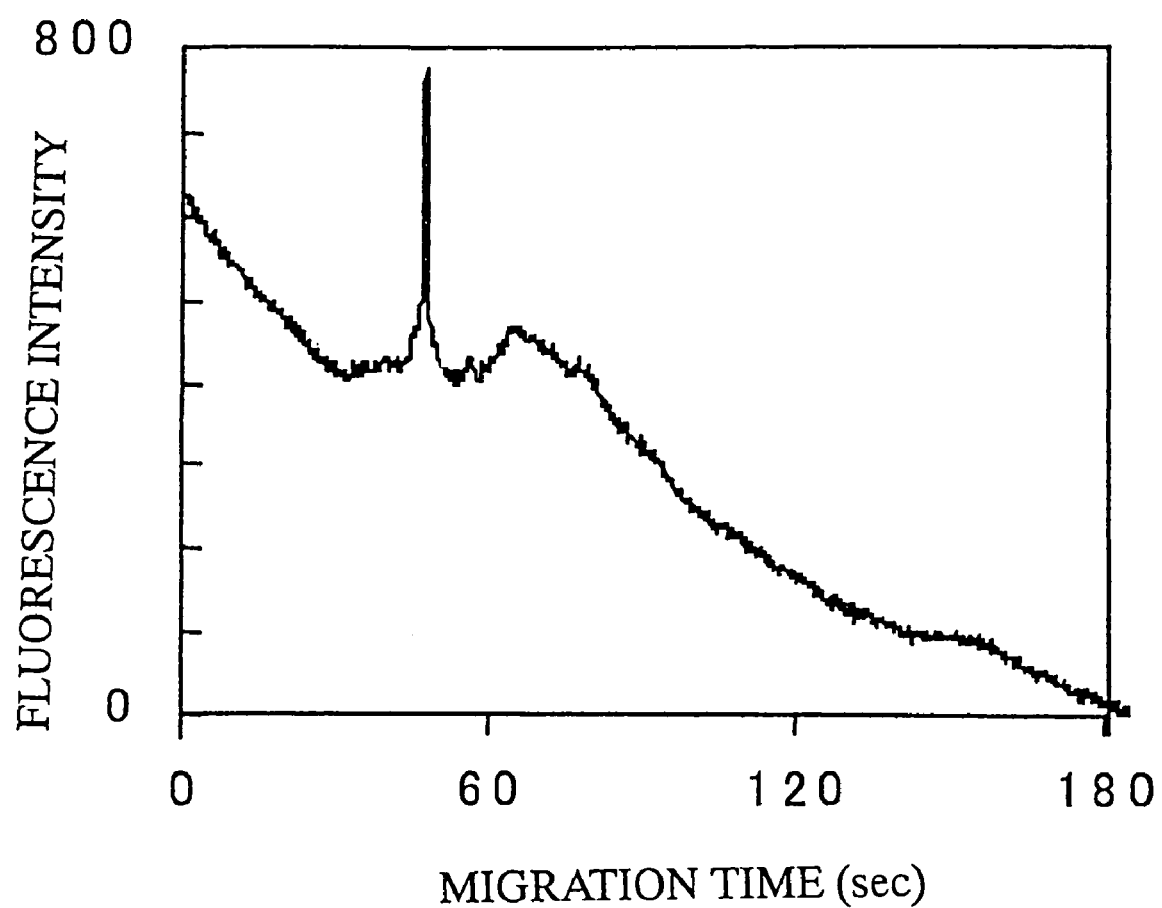
FIG. 26 is a diagram showing the results for studying electrophoretic conditions in a microchip electrophoresis.

In Example 25, the former was M, and P of the latter was MH. As a result, the peak was broadened. (FIG. 26).

From the above, when the conventional polymer solution was used as an electrophoretic buffer, while the migration time of the DNA was improved when using the PP method, there was a limitation in rapid separation in the case of the DNA. On the other hand, in the case of the polymer micelle, it was possible to apply a further higher pressure (Examples 1 to 20), whereby the usefulness of the present polymer micelle was shown.

Although the present polymer micelle alone did not show an effect of DNA separation in the capillary electrophoresis or microchip electrophoresis, the micelle exhibited an effect of size separation of DNA by using the polymer micelle in combination with the PP method. Further, by using an electrophoresis method of the improved PP method, the migration time (about 60 seconds for 10 kbp, about 100 seconds for 15 kbp) further exceeding a maximum detecting rate (about 80 seconds for 10 kbp) with the conventional polymerized polymer solution (for instance, conventional electrophoresis method using a cellulose derivative or a polyacrylamide solution) was accomplished.

INDUSTRIAL APPLICABILITY

According to the electrophoresis method of the present invention, since high separation ability can be obtained rapidly, the method is useful in PCR analysis of gene, cancer gene diagnosis analysis, SNPs analysis by SSCP, VNTR analysis, PCR-RFLP analysis, microsatellite analysis, application to analyses of various diseases such as dementia, muscular dystrophy, heart disease, cardiac infarct, Down's syndrome, infection, diabetes, phenylketonuria and the like, and high-throughput screening analysis of a protein or a sugar chain in proteosome analysis or glycosome analysis. Therefore, there are expected applications to a medical clinical apparatus, and applications to clarification of a biological function, a disease development mechanism and the like.

The invention claimed is:
1. An electrophoretic method comprising:
electrophoresing a sample containing a polymer compound in the presence of an electrophoretic buffer comprising a buffer component; and
a polymerized polymer micelle formed by the steps comprising:
dispersing into an aqueous medium a block copolymer represented by the general formula (1);

HPLS-HPBS-PLZA     (1)

wherein HPLS is a hydrophilic polymer segment, HPBS is a hydrophobic polymer segment, and PLZA is a polymerizable group having an ethylenically unsaturated double bond, and polymerizing the block copolymer.

2. The electrophoretic method according to claim 1, wherein the technique of electrophoresis is capillary electrophoresis, microchip electrophoresis or nano-chip electrophoresis.

3. The electrophoretic method according to claim 1, wherein the technique of electrophoresis is capillary electrophoresis, comprising the steps of:
(a) injecting the sample containing a polymer compound into a capillary by electric injection at 1 to 30 kV for 1 to 60 seconds, or pressurizing injection, to migrate the polymer compound under an electrophoretic electric field capable of separating the polymer compound; and
(b) pressurizing inside the capillary, and migrating the polymer compound by an electrophoretic electric field.

4. The electrophoretic method according to claim 1, wherein the technique of electrophoresis is microchip electrophoresis wherein a microchip comprises a loading channel, and a separating channel intersecting with the loading channel, wherein a sample reservoir is provided on one end of die loading channel, and an outlet is provided on the other end of the loading channel, the electrophoretic method comprising the steps of:
(a) supplying the sample containing a polymer compound to the sample reservoir;
(b) pressurizing the loading channel, thereby migrating the polymer compound in the sample reservoir to the intersecting portion of the loading channel and the separating channel; and
(c) pressurizing the separating channel, and migrating the polymer compound by an electrophoretic electric field in the separating channel.

5. The electrophoretic method according to claim 1, further comprising the step of detecting the electrophoresed polymer compound.

6. A capillary electrophoresis method comprising:
(a) performing said electrophoresis method in the presence of an electrophoretic buffer comprising a buffer component; and a polymerized polymer micelle formed by the steps comprising:
dispersing into an aqueous medium a block copolymer represented by the general formula (1):

HPLS-HPBS-PLZA     (1)

wherein HPLS is a hydrophilic polymer segment, HPBS is a hydrophobic polymer segment, and PLZA is a polymerizable group having an ethylenically unsaturated double bond, and polymerizing the block copolymer,
(b) injecting a sample containing a polymer compound into a capillary by electric injection at 1 to 30 kV for 1 to 60 seconds, or pressurizing injection at 0.2 to 5 kPa for 2 to 60 seconds, to migrate the polymer compound under an electrophoretic electric field capable of separating the polymer compound; and
(c) pressurizing at 0.2 to 5 kPa for 2 to 60 seconds, and migrating the polymer compound by an electrophoretic electric field.

7. A microchip electrophoresis method comprising:
(a) performing said microchip electrophoresis method in the presence of an electrophoretic buffer comprising a buffer component; and
a polymerized polymer micelle formed by the steps comprising:
dispersing into an aqueous medium a block copolymer represented by the general formula (1):

HPLS-HPBS-PLZA     (1)

wherein HPLS is a hydrophilic polymer segment, HPBS is a hydrophobic polymer segment, and PLZA is a polymerizable group having an ethylenically unsaturated double bond, and polymerizing the Hock copolymer,
(b) supplying a sample containing a polymer compound to the sample reservoir;
(c) pressurizing the loading channel at 5.5 to 7 kPa for 0.1 to 5 seconds, thereby migrating the polymer compound in the sample reservoir to the intersecting portion of the loading channel and the separating channel; and
(d) pressurizing the separating channel at 1 to 10 kPa for 0.1 to 5 seconds, and migrating the polymer compound by an electrophoretic electric field in the separating channel,
wherein a microchip comprises a loading channel, and a separating channel intersecting with the loading channel, wherein a sample reservoir is provided on one end of the loading channel, and an outlet is provided on the other end of the loading channel.

8. The electrophoretic method of claim 1, 6 or 7, further comprising adding a low-molecular polymerizable monomer to the block copolymer and polymerizing the block copolymer.

9. The electrophoretic method according to claim 8, wherein the polymer constituting HPLS is selected from the group consisting of polyethylene glycol, polyvinyl alcohol, poly(meth)acrylic acid, polyvinyl pyridine, polyacrylamide, polydimethyl acrylamide, and polymethlyl vinyl ether, and wherein the polymer constituting HPBS is selected from the group consisting of polylactide, polyglycolide, poly(butyrolactone), poly(valerolactone), polypropylene glycol, poly($\alpha$-amino acid), poly(methyl methacrylate), poly(ethyl methacrytate), polystyrene, poly($\alpha$-methylstyrene), polyisoprene, polybutadiene, polyethylene, polypropylene and polyvinyl acetate.

10. The electrophoretic method of claim 1, 6 or 7, wherein HPLS is polyethylene glycol, and wherein HPBS is selected from the group consisting of polylactide, polyglycolide, poly(butyrolactone), poly(valerolactone), polypropylene glycol, and poly($\alpha$-amino acid).

11. The electrophoresis method of claim 1, 6 or 7, wherein said buffer components is selected from the group consisting of Tris-glycine buffer, Tris-borate buffer, Tris-hydrochioric acid buffer, Tris-tricine buffer, Tris-sodium hydrogen phosphate buffer, and Tris-borate-EDTA buffer.

12. The electrophoresis method of claim or 1, 6 or 7, which further comprises sodium dodecylsulfate (SDS).

13. The electrophoresis method of claim 1, 6 or 7, wherein said electrophoretic buffer further comprises Triton X-100, $\epsilon$-aminocaproic acid, 3-[(3-cholamidopropyl)-dimethylammonio]-1-propanesulfonate (CHAPS), 6 to 8 M urea, tetramethylethylenediamine (TEMED), and hexyltrimethylaxnrnonium bromide (HTAB).

14. The electrophoresis method of claim 1, 6 or 7, which said electrophoretic buffer has a pH of 2 to 9.

* * * * *